United States Patent
Xiao et al.

(10) Patent No.: US 6,930,479 B2
(45) Date of Patent: Aug. 16, 2005

(54) HIGH RESOLUTION SCANNING MAGNETIC MICROSCOPE OPERABLE AT HIGH TEMPERATURE

(75) Inventors: Gang Xiao, Barrington, RI (US); Benaiah D. Schrag, Providence, RI (US)

(73) Assignee: Brown University Research Foundation, Providence, RI (US)

( * ) Notice: Subject to any disclaimer, the term of this patent is extended or adjusted under 35 U.S.C. 154(b) by 0 days.

(21) Appl. No.: 10/493,841
(22) PCT Filed: Mar. 7, 2003
(86) PCT No.: PCT/US03/06973
§ 371 (c)(1),
(2), (4) Date: Apr. 28, 2004
(87) PCT Pub. No.: WO03/076954
PCT Pub. Date: Sep. 18, 2003

(65) Prior Publication Data
US 2004/0239318 A1 Dec. 2, 2004

Related U.S. Application Data
(60) Provisional application No. 60/362,788, filed on Mar. 8, 2002.

(51) Int. Cl.⁷ ............................................. G01N 27/00
(52) U.S. Cl. ....................................... 324/262; 324/244
(58) Field of Search ................................. 324/244, 249, 324/260–262, 522–523, 527, 529, 750, 754–755, 758–759, 763

(56) References Cited
U.S. PATENT DOCUMENTS

| | | | |
|---|---|---|---|
| 5,627,101 A | 5/1997 | Lin et al. | 438/18 |
| 6,118,284 A | 9/2000 | Ghoshal et al. | 324/750 |
| 6,320,391 B1 | 11/2001 | Bui | 324/537 |
| 6,396,261 B1 | 5/2002 | Martchevskii et al. | 324/235 |
| 6,545,492 B1 | 4/2003 | Altmann et al. | 324/754 |
| 6,571,183 B1 | 5/2003 | Wellstood et al. | 702/65 |
| 2002/0033695 A1 | 3/2002 | Xiao | 324/244 |

FOREIGN PATENT DOCUMENTS

EP 0907085 A1 4/1999

OTHER PUBLICATIONS

Panin, Alexey and Shugurov, Artur, "Electromigration–Induced Damage of AU Conductor Lines", Proceedings of the Fifth Russian–Korean International Symposium on Science & Technology, Jun. 26, 2001, pp. 182–186.

*Primary Examiner*—Bot LeDynh
(74) *Attorney, Agent, or Firm*—Harrington & Smith, LLP

(57) ABSTRACT

A scanning magnetic microscope (SMM) (20) includes a current source (27) for imposing an excitation current to a conductor-under-test (CUT) (70) and, if applicable, a reference current to a proximally located reference conductor (72). During accelerated testing, the SMM (20) corrects thermal drift of the CUT (70) via the reference conductor (72). A sensor (21) may be cooled by a heat sink (31) such as a pump (33) directing an airstream or a coldfinger (80). The sensor may switch from a contact to a non-contact mode of scanning the CUT (70). The SMM (20) and methods are useful for measuring electromigration in a CUT (70) as it occurs, for assembling the images into time lapsed representations such as a shape of the CUT (70), for measuring electromigration as a function of a cross sectional area of a wire under a dielectric material (DM) (78), for determining electrical parameters of the CUT (70), and for optimizing a thickness of a DM (78) over a CUT (70). The SMM (20) and methods are further useful for measuring morphological changes in a CUT (70) due to other stressing conditions, such as temperature, excitation current, physical stress(es), hostile environment, aging, semiconductor "burn-in", or irradiation.

37 Claims, 15 Drawing Sheets

HIGH RESOLUTION SCANNING MAGNETIC MICROSCOPE OPERABLE AT HIGH TEMPERATURE

PRIORITY STATEMENT

This application claims priority to International Patent Application No. PCT/US03/06973, filed on Mar. 7, 2003, and to U.S. Provisional Patent Application No. 60/362,788, filed on Mar. 8, 2002, through the referenced PCT application.

STATEMENT OF GOVERNMENT RIGHTS

This invention was made with government support under the National Science Foundation, award no. DM19960292. The government may have certain rights in this invention.

TECHNICAL FIELD

This invention is broadly concerned with a magnetic microscope and a technique for high temperature imaging of electrical current densities with sub-micron resolution, especially for the analysis of electromigration, using magnetic tunneling junction sensors or giant magnetoresistive sensors.

BACKGROUND

Electromigration (EM) failure remains one of the most challenging problems facing the semiconductor industry. EM is the process by which a large electrical current flowing through a fine conducting wire or element can cause atomic diffusion in the direction of the electron flow. This phenomenon is thermally activated, and becomes exponentially stronger at higher temperatures, as it depends as a power-law on the current density. EM is one of the most common failure mechanisms in integrated circuits (IC), which operate at high current densities (approximately 100 kA/cm$^2$) and elevated temperatures (greater than 50° C.). Physically, the momentum transfer between electrons and the atomic lattice causes atoms to diffuse, creating vacancies or "voids" in the fine wire. These voids can then move, combine, and divide, exhibiting surprisingly complex dynamics that is not well understood. The process of diffusion eventually causes the fine wire to break and fail. Even a small number of EM-induced defects may cause an IC to cease to function. Future ICs promise to operate with higher current densities and higher operating temperatures, as the industry trend toward smaller conductors continues to progress. As this trend continues, the significance of the EM failure mechanism will continue to grow.

EM is notoriously complex and depends on a large number of factors: the composition, microstructure, and dimensions of the wires, the ambient operating conditions, the thickness and composition of any overlayer, etc. Under typical operating conditions, EM can take months or years to become a significant problem in IC operation. Therefore, virtually all EM testing is conducted under accelerated testing conditions, which feature higher temperatures (>150° C.) and much higher current densities (0.5–5 MA/cm$^2$) than are found in typical operational conditions for ICs. The results can then be extrapolated to more typical operating parameters. Because EM is such a difficult problem, with such far-reaching impacts on IC fabrication, there are many groups in both academia and industry attempting to understand this phenomenon.

Methods for Studying Electromigration

Currently there are several techniques for studying EM, which include mean-time-to-failure measurements, resistometric evaluations, noise measurements, and microscopy. Unfortunately, each of these techniques fails to adequately describe EM, as described below.

Mean-time-to-failure (MTF) measurements provide a quantitative measure of IC resistance to EM, but offer no insight into the actual dynamics of the EM process. These measurements stress many conductors until a certain failure condition is achieved. Once failure conditions are achieved, statistical analyses provide insight into predicting IC failure from EM.

Both resistometric evaluations and noise measurement techniques give precise information about the electrical properties of conductors at various points in time, but the results of such tests are often difficult to interpret, and cannot provide any information about the micro-structural changes occurring in the sample.

Microscopy techniques have used both scanning electron microscopy (SEM) and transmission electron microscopy (TEM). SEM and TEM provide microstructural imaging of samples damaged by EM. Due to sample preparation requirements, both SEM and TEM techniques are destructive and can only be used on samples not "buried" by a dielectric overlayer. The value of SEM and TEM is thus limited because all ICs include a passivation layer to protect the active layer(s), and this passivation has a critical influence on the EM process. In addition, these techniques can require elaborate and time-consuming sample preparation procedures, such as the use of a focused ion beam (FIB) to cleave samples for TEM studies. Another drawback to these techniques is that they provide little quantitative information about the thickness of EM-induced voiding.

Other technologies presently available have been unfulfilling to date in efforts to gain more information about EM.

Magnetic Sensing Technologies

A physical object may generate a magnetic-field (H) that can be sensed near the surface of the object. Using magnetic sensing technology, an "image" of the magnetic field distribution may be obtained. Such images can be spatially microscopic and weak in field strength. Nevertheless, these images reveal important signatures of inherent electrical and magnetic processes within the objects. For example, the magnetic image of a magnetic thin film discloses its internal magnetic domain structure. The electrical currents inside an IC chip generate external magnetic fields, which not only contain information about the spatial variation of current density, but also the frequencies with which various components on a chip are operating. A type II superconductor also creates threading magnetic flux lines that may be imaged, whose structure and dynamics reveal fundamental properties.

There are various techniques presently used to detect magnetic properties at a surface of a sample. These have included electron holography, scanning electron microscopy with polarization analysis (SEMPA), magneto-optical microscopy, and scanning magnetic microscopy (SMM).

Electron holography and SEMPA require high vacuum operation and delicate sample preparation. Both of these techniques offer static field images with good spatial resolution. However, the instruments are expensive and demand great technical skill to operate. The magneto-optical microscope is a relatively simple system and suitable for time-resolved imaging. However, its field sensitivity and spatial resolution are poor. It should be noted that many of these techniques are sensitive to magnetization, rather than stray field, which makes them unsuitable to the application at hand.

Scanning magnetic microscopes have a magnetic sensing element, such as a SQUID or Hall effect element, which is physically scanned relative to a sample to obtain a local field image. Though very sensitive, a SQUID probe is poor in resolution (~30 $\mu$m), and requires cryogenics to operate. A Hall probe can operate under ambient conditions, but its sensitivity is low. Microscopes equipped with a magnetic tip, using a technique called magnetic force microscopy (MFM), can only measure the gradient of a magnetic field, and have not yet demonstrated their usefulness for application to current imaging.

The result is that no successful technique for high resolution, time-lapse or real time EM imaging is commercially available. The trend towards reduced IC feature size and a large number of metal layers mandates the development of a commercially viable technique that is suitable for EM imaging.

SUMMARY OF THE PREFERRED EMBODIMENTS

The foregoing and other problems are overcome, and other advantages are realized, in accordance with the presently preferred embodiments of these teachings. In accordance with one aspect of this invention, a method for measuring a change over time in the morphology of a conductor-under-test (CUT) is presented. This method includes passing an excitation current through a conductor-under-test (CUT), measuring a first two dimensional (2D) magnetic field map associated with the CUT at a first time with a scanning magnetic sensor, measuring a second 2D magnetic field map associated with the CUT at a second time, and converting the first magnetic field map to a first current density image and the second magnetic field map to a second current density image, each image representing a morphology and current distribution of the CUT with sub-micron resolution.

In another aspect of this invention, a scanning magnetic microscope (SMM) includes a first circuit for passing an excitation current through a conductor-under-test (CUT) and a second circuit for passing a reference current through a reference conductor wherein the reference conductor defines a known shape. The SMM also includes a magnetic field sensor for imaging a two-dimensional magnetic field map generated by the CUT. This sensor is capable of sub-micron resolution, though it may be advantageous to use such high resolution only at particular areas of a specimen, such as those where the CUT indicates damage. The best resolution occurs when the sensor is in close proximity with a surface of the CUT or a dielectric material overlayer. The SMM also includes means for moving the sensor relative to the CUT and the reference conductor, software for correcting a thermal drift of the CUT; and software for converting the two dimensional magnetic field map to a current density image.

According to another aspect of the invention, a method for determining the width (w) of a conductor-under-test (CUT) disposed under a dielectric material is disclosed. This method includes determining the depth of the CUT from a surface of a dielectric material, passing an electrical current through the CUT, measuring a magnetic field associated with the electrical current with the magnetic sensor at a height (h) of the sensor above the CUT, measuring a peak-to-peak spacing ($d_{PTP}$) of the spatial magnetic field profile across the width direction of the CUT; and determining the width using a relation that is mathematically equivalent to $d_{PTP}=\sqrt{4h^2+w^2}$.

The present invention also includes a method for determining a normalized electrical current density in a wire. This method includes disposing a surface of the specimen adjacent to a scanning magnetic sensor, passing an excitation current through a wire disposed beneath the surface of the specimen, measuring a first 2D magnetic field map with the scanning magnetic sensor at a height $z_1$ above the surface, measuring a second 2D magnetic field map with the scanning magnetic sensor at a height $z_2$ above the surface, wherein $z_2>z_1$. This method was a deconvolution algorithm to automatically determine d and z, which are used as parameters, to create a normalized current density image as above.

An important aspect of the invention is a method for representing an evolution over time of electromigration within a conductor-under-test (CUT). This method includes passing a reference current through a reference conductor, passing an excitation current through a CUT at a first time and at a second time, measuring a first sensed 2D magnetic field map associated with the CUT at the first time with a scanning magnetic sensor, measuring a second sensed 2D magnetic field map associated with the CUT at the second time, aligning each of the first and the second sensed magnetic field maps relative to the reference conductor, converting the first and second sensed magnetic field maps to a first and a second current density images, and displaying the first and second current density images in sequence. A plurality of such images may be displayed as a movie to show graphic detail of the time evolution of electromigration.

Another important aspect of the invention is a method of measuring electromigration evolution as function of a cross sectional area of a wire. This method includes providing a wire that defines a first cross sectional area and a second cross sectional area that differs from the first, and providing a dielectric material that defines a substantially uniform thickness over the wire. It further includes passing an excitation current through the wire, measuring a first 2D magnetic field map associated with the wire's first cross sectional area and a second 2D magnetic field map associated with the wire's second cross sectional area. The method further includes converting the first magnetic field map to a first current density image and the second magnetic field map to a second current density image, each image representing electromigration induced morphology and current distribution in the wire.

Another important aspect of this invention is a method of measuring electromigration as a function of a thickness of a dielectric layer overlying a wire, which may be used for determining an optimal thickness for a wire. This method includes providing a wire that defines a substantially uniform thickness, and providing a dielectric material defining a first thickness over a first portion of the wire and a second thickness over a second portion of the wire. The method further entails passing an excitation current through the wire, measuring a first 2D magnetic field map associated with the first portion of the wire and a second 2D magnetic field map associated with the second portion of the wire, and determining whether electromigration induced morphology has occurred at the first portion or at the second portion of the wire.

Another important aspect of this invention is a method for measuring the evolution in the morphology of a CUT as a result of any stressing which requires the CUT to experience elevated temperatures, such as electromigration, integrated circuit "burn-in testing", thermal stressing, etc., and the methods involved in accounting for high-temperature artifacts and complications involved therein.

Another aspect of the present invention is a method for determining whether an electrical conductor has delaminated from a substrate. This method includes providing a substrate and a conductor, passing an electrical current through the conductor, measuring a first two dimensional magnetic field map associated with the conductor being bonded to the substrate at a first time with a scanning magnetic sensor, and measuring a second two dimensional magnetic field map associated with the conductor at a second time. The method further includes converting the first and second magnetic field maps to a first and second current density maps, and comparing the current density maps to determine whether the conductor has delaminated.

Yet another very important aspect of this invention is a method for measuring a change over time in the morphology of a CUT, such change in morphology can be due to one or more stressing conditions such as: DC electrical current in CUT, temperature that is higher than ambient temperature, aging, environmental condition(s) such as moisture and pressure, intrinsic or extrinsic physical stress, semiconductor "burn-in" testing, or irradiation as with particle beams or light. This method entails applying one or more than one of the stressing conditions above to the CUT. The method further entails passing an excitation current through the CUT, measuring a first 2D magnetic field map associated with the CUT at a first time and a second 2D magnetic field map associated with the CUT at a second time, and converting the first magnetic field map to a first current density image and the second magnetic field map to a second current density image, each image representing morphology and current distribution in the CUT under the influence of various conditions listed above at a given time. If needed, the thermal drift can be corrected using the method of reference conductor or local thermometry.

BRIEF DESCRIPTION OF THE DRAWINGS

The foregoing and other aspects of these teachings are made more evident in the following Detailed Description of the Preferred Embodiments, when read in conjunction with the attached Drawing Figures, wherein.

DETAILED DESCRIPTION OF THE PREFERRED EMBODIMENTS

Figure 1:
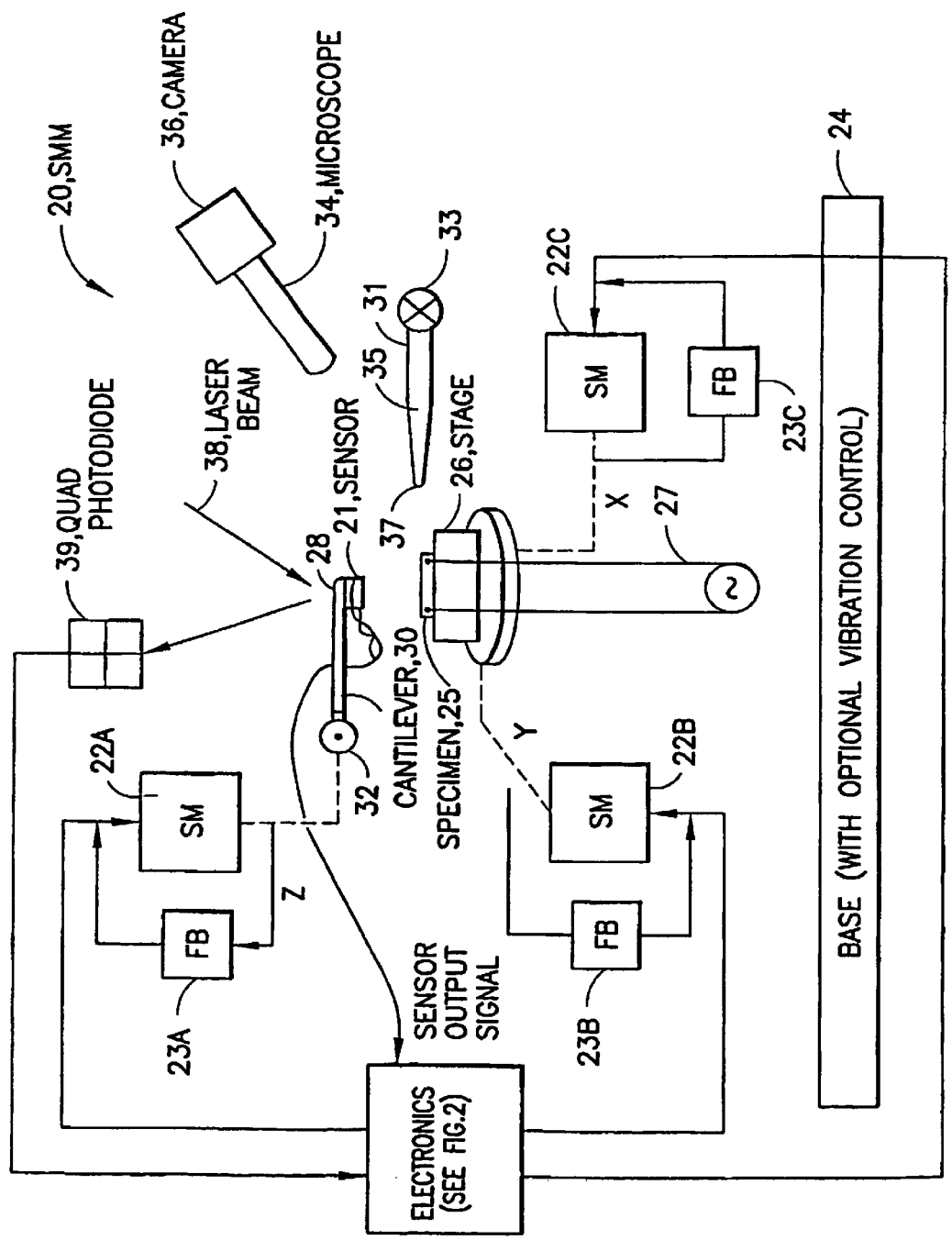
FIG. 1 is a block diagram of a scanning magnetic microscope (SMM) in accordance with the preferred embodiment of the invention.
Figure 2:
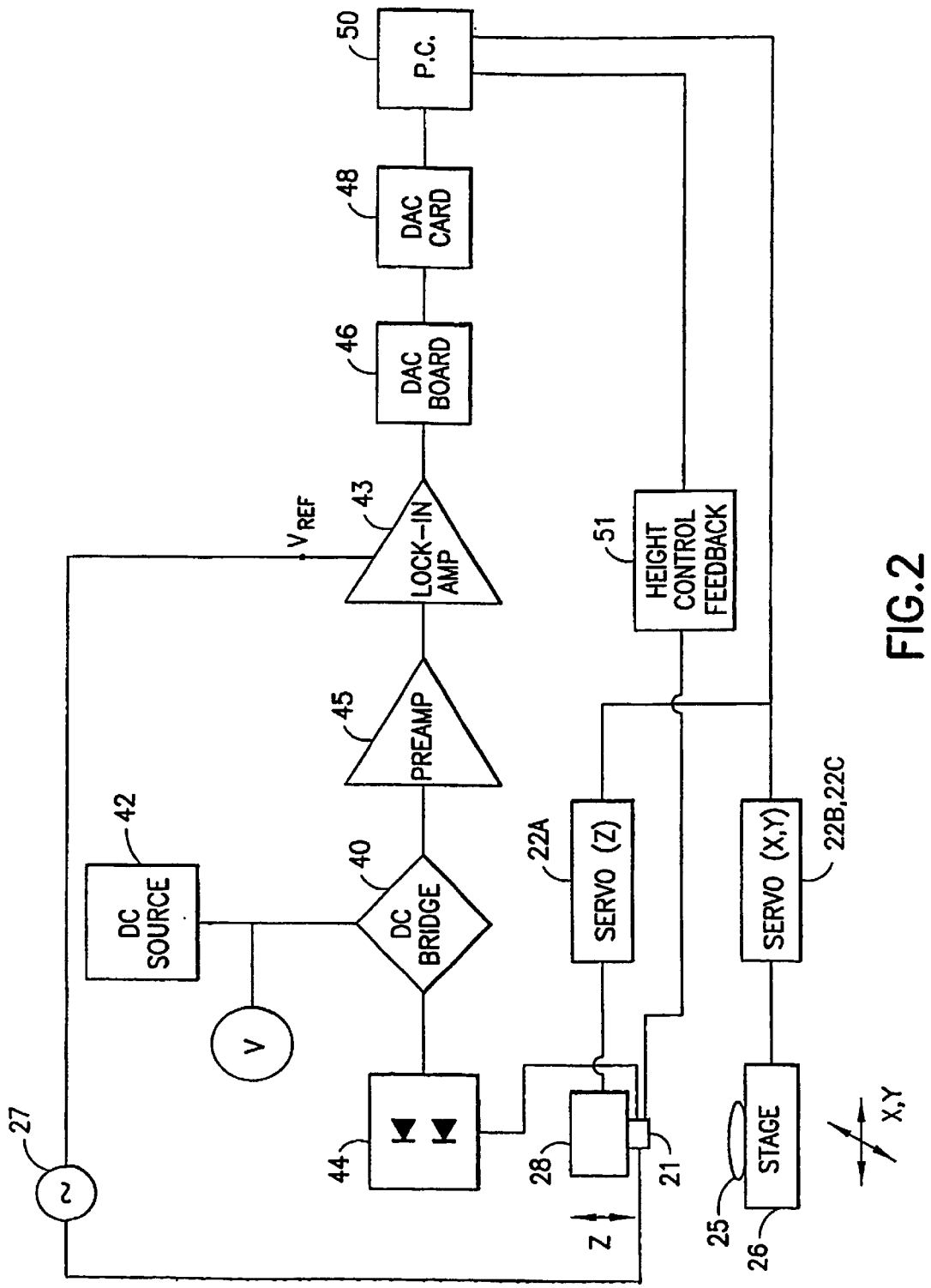
FIG. 2 is an electrical block diagram of certain of the electronics of FIG. 1.

In the preferred embodiment shown in FIGS. 1–3, the scanning magnetic microscope (SMM) 20 of this invention can be broken down into three main components: a translation stage and motion controller which moves a magnetic sensor 21 relative to a specimen 25 that may be mounted on a stage 26, and electronics built around the sensor 21. The magnetic sensor 21 may include capacitance gauging or similar means to control a height of the sensor 21 above a surface of the specimen 25 or other such positional control of the sensor. Preferably, the stage 26 is heated such as by a heating element and temperature controller interfaced to a P.C. 50 so that the temperature of the specimen 25 may be controlled. In a presently preferred embodiment, three Aerotech series 300 linear translation servo-motors 22A–22C with spatial resolution of 0.1 micron move the specimen 25 relative to the sensor 21. The specimen 25 is mounted via vacuum, an adhesive or a fixture on a two-axis (x, y) translation stage 26 that is itself moved by servo-motors 22B, 22C. The sensor 21 is fixed to a mount 28 that translates vertically (z) using the third stage 22A, and may be suspended over the specimen 21 by a cantilever 30 movable about a pivot 32, or by a vertical shaft. Each of the servo-motors 22A, 22B, 22C include linear encoders 23A, 23B, 23C or an equivalent absolute positioning capability. A current source 27 is used to drive the excitation current to the specimen 25 at, for example, several to hundreds of kHz, and provides a reference frequency for lock-in amplification, discussed below. Preferably, the current source 27 provides an AC excitation current to the specimen 25 that is referenced to a DC lock-in amplification. Such a current source can also supply a substantial direct-current (DC), as in electromigration, to stress the CUT, in addition to the alternating-current (AC) for measurement. The stage 26 is built on a heavy base 24 or a vibration-isolation stage to reduce vibration. An optional wide-angle zoom optical microscope 34 may be used to inspect the position of the sensor 21 relative to the specimen surface 64. Preferably, the sensor 21 rides along the specimen surface 64 (see FIG. 3). A laser, in conjunction with a quad photodiode 39, may be used to precisely control the height of the sensor 21 by sensing reflection of the laser beam 38 from a reflective surface on the back side of the mount 28. A heat sink 31 may be thermally coupled to the sensor 21 to minimize heat build-up within the sensor 21 during high temperature operation. In one embodiment, a pump 33 directs a gas, such as air, along a tube 35 defining a discharge end 37, wherein the discharge end 37 is located proximal to the interface between the sensor 21 and the specimen 25 and provides a flow of gas that removes heat from the interface region. A coldfinger can also be used to cool the sensor.

In one embodiment, the sensor 21 is a GMR spin-valve read/write head used in magnetic hard drives. A DC source 42 provides a sense current of ~5 mA to the sensor 21. The sensor 21 is integrated into an optional Wheatstone bridge 40 and protected from voltage surges by a protection block 44 that includes two crossed Schottky diodes and a shunting resistor. In addition, the sensor 21 is preferably grounded at all times except during data acquisition to avoid damage due to electrostatic discharge. The output of the bridge 40 is passed through a differential preamplifier 45 and into a lock-in amplifier 43. The spatial resolution of the magnetic sensor 21 is sub-micron in both dimensions (x, y), and no worse than 0.1 $\mu$m in the primary scan direction. Magnetic images may be taken by rastering the sensor 21 across the sample, preferably while in physical contact or in close proximity. A data acquisition board 46, 48 allows rapid collection of data, and the entire process is automated and controlled using a computer 50, such as a P.C. running LabVIEW™ software. The signal-to-noise ratio of this technique is dependent on various parameters, including but not limited to: the current density in the specimen 25; lock-in parameters; the scanning (rastering) speed; the modulation frequency; and, the thickness of a dielectric material overlayer, if any, between the sensor 21 and current carrying wires 70, 72 of the specimen 25. Using typical modulation currents with amplitudes of 2–3 mA, a signal to noise ratio greater than 150:1 is obtained. Where the sensor 21 includes means for controlling height from the specimen 25, such as a capacitance gauge, a feedback loop 51 preferably reports measured height back to the P.C. for integration with other measured data.

One presently preferred embodiment of an MTJ sensor 21 is fabricated in a high vacuum sputtering system, and offers sub-micron spatial resolution, a non-hysteretic linear response, and operation at high temperature.

Figure 3A:
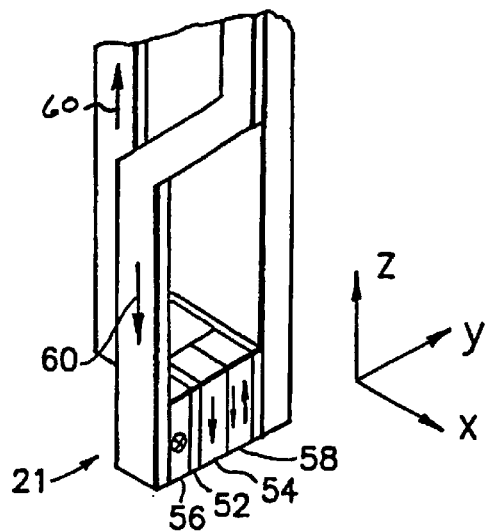
FIG. 3A is a perspective view of a MTJ sensor positioned to scan in the x-y plane.

In this embodiment and referring to FIG. 3A, the fabrication process begins with the high-vacuum sputtering deposition of a multilayer thin film at room temperature. The tunnel barrier layer 52 of $Al_2O_3$, which separates the pinned layer 54 from the free layer 56, is formed by plasma or natural oxidation of an Al layer with thickness 6–20 Å in 100 mTorr of $O_2$ for 2–7 min, or by a combination of the two. The pinned layer 54 is a ferromagnetic (FM) thin film, typically permalloy or Co, which is exchange biased by an adjacent antiferromagnetic (AFM) film (e.g., FeMn and PtMn) 58. The free layer 56 is an unbiased soft ferromagnetic thin film located on the opposite side of the barrier layer 52. The sensor 21 preferentially exhibits a linear response, and this is accomplished by making the pinning direction perpendicular to the easy-axis of the free layer 56. After depositing the MTJ multilayer sensor 21 on a silicon wafer substrate (not shown), the magnetic hysteresis loop of the sensor 21 can be measured with a SQUID magnetometer, from which one can observe hysteresis sub-loops of the different magnetic layers. The shape and field offset of each loop is used to obtain information about the quality of layers and interfaces. A sense current 60 passes through the multilayer body and a magnetic field along the z axis is measured.

Figure 3B:
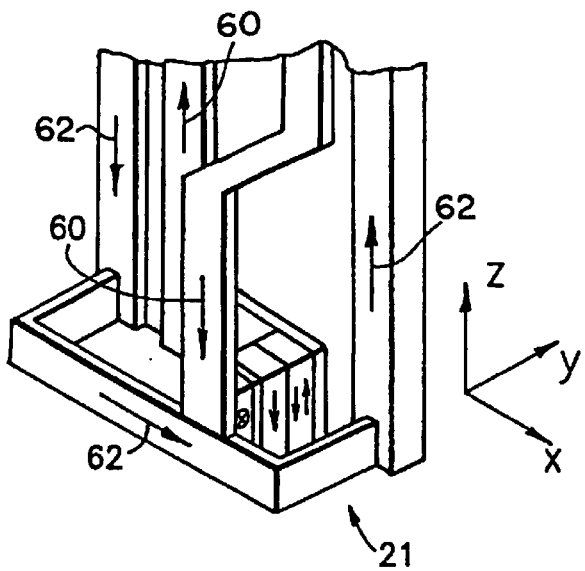
FIG. 3B is similar to FIG. 3A but the sensor includes a biasing current that imposed a biasing magnetic field.
Figure 3C:
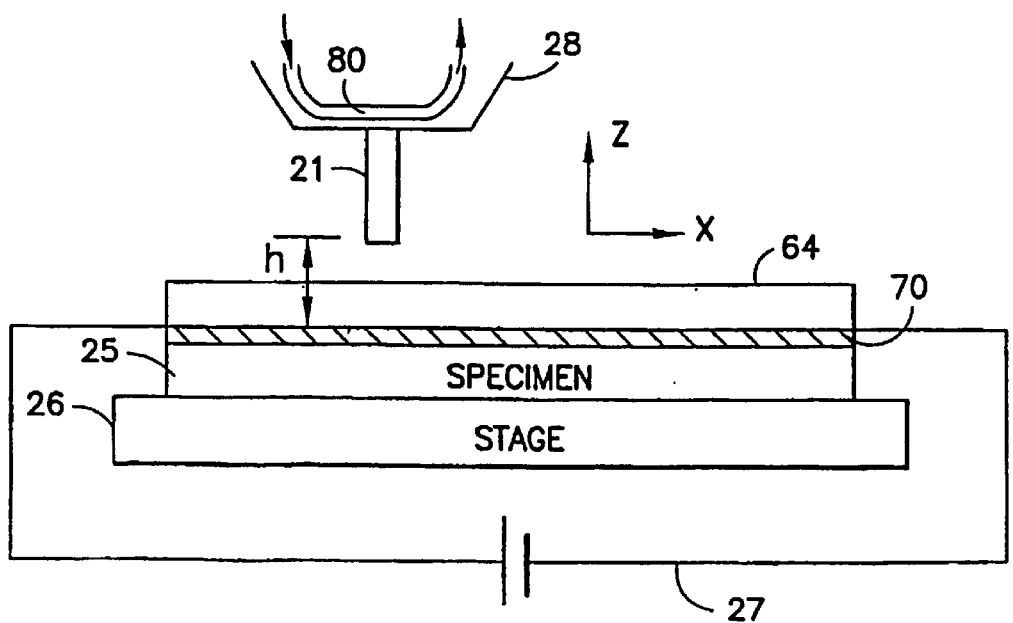
FIG. 3C is a block diagram showing a sensor at a height h above a conductor embedded within a specimen.

FIG. 3B shows a sensor 21 similar to that of FIG. 3A, but with an additional biasing current 62 imposed parallel to the scanning plane (x-y plane). This biasing current 62 generates a biasing magnetic field. A sensor 21 such as those of FIG. 3A or 3B is shown in FIG. 3C relative to a specimen 25, but with coldfinger 80 passing through the mount 28 and positioned to draw heat from the sensor 21 (i.e., thermally coupled thereto). This coldfinger 80 acts as a heat sink for the sensor to protect it from absorbing excessive heat from accelerated testing. The cold finger 80 is preferably in contact with a silicon wafer (not shown) on which the sensor is built, and preferably circulates a cryogenic or chilled fluid. The specimen 25 as depicted includes a layer of dielectric material 78 overlying the conductor 70. The sensor is mounted to the stage 26 and an excitation current 27 is passed through the conductor 70. During accelerated testing such as when a stressing current is used as the excitation current 27, the conductor 70 and the specimen tend to heat up rapidly. During conditions of high specimen temperature, the sensor 21 may be scanned across the x-y plane while spaced a distance h from the conductor 70 and a non-zero distance z from the surface 64 of the specimen (non-contact mode). The particular sensors 21 described herein are capable of measuring magnetic fields associated with a conductor 70 buried under a layer of dielectric material 7S with sufficient resolution to image morphology of electromigration within the conductor 70.

Figure 4A:
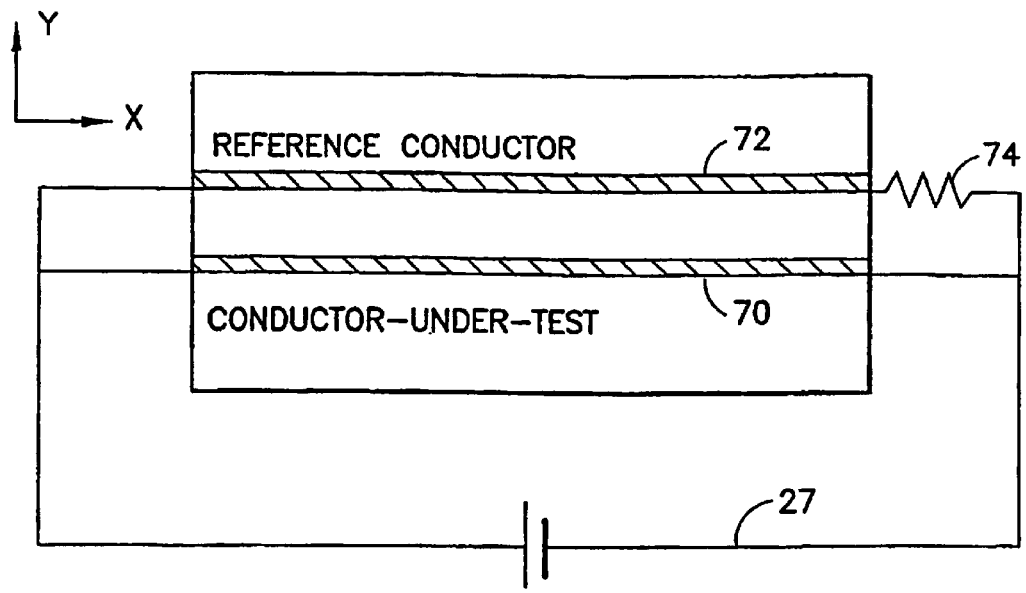
FIG. 4A is a block diagram showing a specimen defining a conductor-under-test and a reference conductor, connected in parallel to the current source.

One of the difficulties in electromigration imaging is that sensors are generally not operable at the high temperatures (>150° C.) typically associated with accelerated testing conditions, at least not with precision sufficient to resolve electromigration as it occurs. At high temperatures, the physical position of the wire, or conductor-under-test (CUT), may vary as much as 2 microns per degree centigrade. This phenomenon is known as thermal drift, and must be accounted for in order to portray only electromigration alone, apart from thermal drift. In accordance with an aspect of this invention, thermal drift may be corrected by using a reference conductor. FIG. 4A depicts a reference conductor 72 that is disposed within the same specimen 25 as the CUT 70. Most trace lines in an integrated circuit (IC) proximal to a CUT 70 can serve as a reference conductor 72. The reference conductor 72 may be in parallel with or separate from the CUT 70, and be of known dimensions, preferably on the same order as the CUT 70. The reference conductor 72 should follow the contours of the CUT 70 in a known fashion, and should ideally contain a significant number of non co-linear reference points, such as is found in a serpentine pattern, for correction in both lateral directions. The reference conductor 72 preferably is protected from morphological change due to, for example, electromigration, and the arrangement of FIG. 4A uses a resistor 74 in series with the reference conductor to reduce the current passing through the reference conductor 72 (reference current) as compared to the stressing current passing through the CUT 70 when the two conductors 70, 72 are in parallel with the same current source 27. The resistor 74 may be a traditional component resistor, or merely a longer circuit pathway through the reference conductor 72 as compared to the CUT 70. Software and circuitry are included as components of the SMM 20 for the purpose of recognizing magnetic field maps and converting to current density images associated with the reference line 72 and the CUT 70, and for automatically correcting for thermal drift.

Figure 4B:
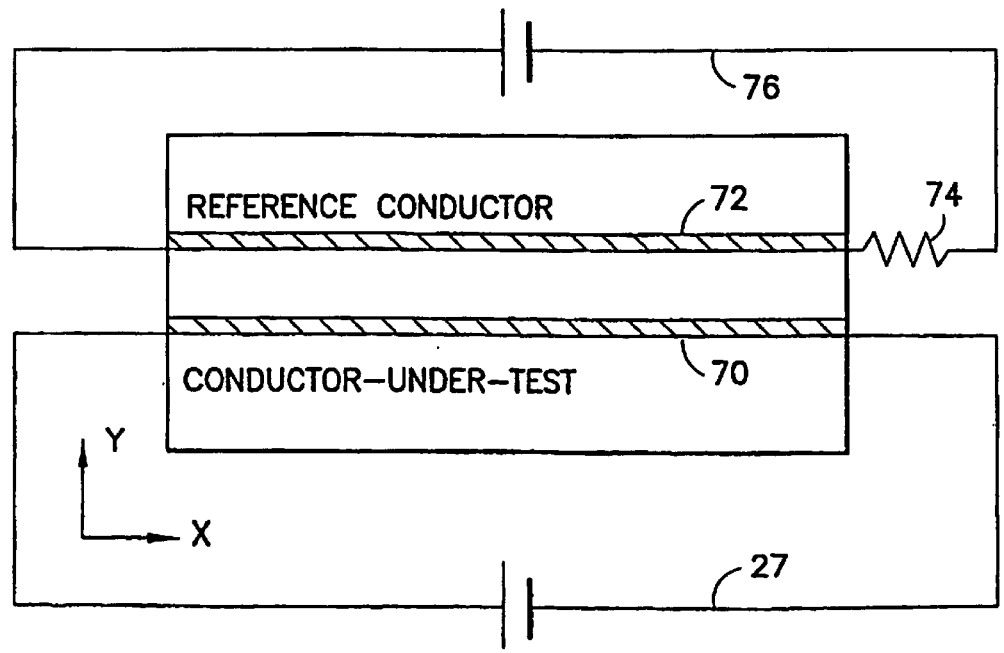
FIG. 4B is a block diagram showing a specimen defining a conductor-under-test and a separate reference conductor connected to separate current sources.

The arrangement of FIG. 4B depicts an alternative arrangement, wherein the reference conductor 72 is tied to a reference current source 76 that is separate form die excitation current source 27 that drives the CUT 70. Preferably, the dimensions and temperature-coefficient of resistance for the reference conductor 72 are known so that its resistance may be measured and a localized temperature calculated by separate circuitry and software during the time of scanning the conductor 70 by the sensor 21. In this manner, the reference conductor 72 may act as a thermometer for each data point, and the reference conductor 72 may be in parallel with the CUT 70 as in FIG. 4A or on a separate circuit as in FIG. 4B. In the embodiment of FIG. 4B, the excitation current source 27 provides a greater current than that provided by the reference current source 76, so that the resistor 74 may or may not be necessary. Each of FIGS. 4A–4B is viewed in the x-y plane, wherein the sensor scans the conductors 70, 72 in the y-direction (i.e., across the width of the conductors 70, 72). The sensor 21 is then shifted by a small increment in the x-direction and repeats the y-direction scanning. This scanning process continues until the entire area of interest pertaining to the CUT 70 is scanned. Data is gathered by the sensor 21 for both the CUT 70 and the reference conductor 72. With a low reference current, the reference conductor 72 does not suffer from electromigration or morphological change, while the CUT may undergo morphological change. Since both conductors share the same thermal drift, the relative average separation of the two conductors remains unchanged, providing a correction method of thermal drift effect. The morphological change in the CUT 70 due to electromigration can be distinguished from thermal drift, which should be present in adjacent areas of the Cut 70 and the reference conductor 72 to the same extent. The magnetic fields associated with the reference conductor 72 and the CUT 70 may be sensed by a single sensor 21 at different times via scanning the sensor 21, or simultaneously by a pair or an array of sensors 21 to speed up the scanning process.

Figure 5A:
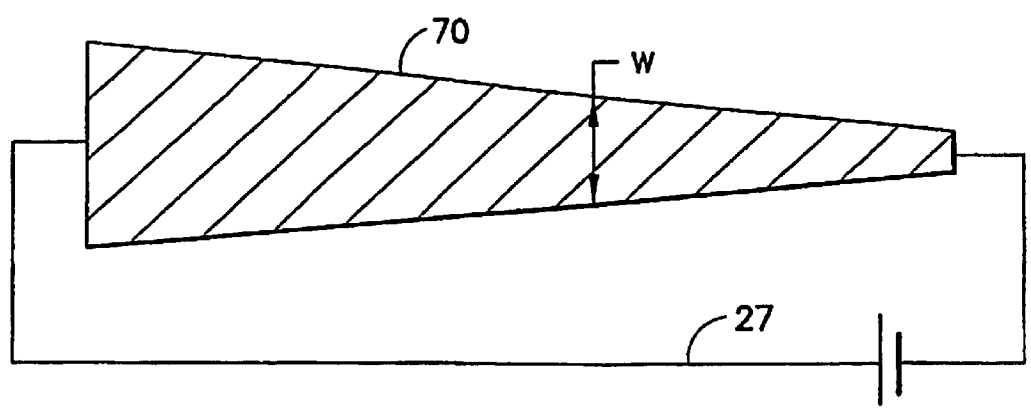
FIG. 5A is a simplified block diagram showing a wire of variable width w under test.

FIG. 5A is a simplified diagram of a CUT 70 defining a variable width w that may be employed to measure electromigration as a function of wire width. In the past, wires of varying widths were subjected to accelerated testing, each covered with a substantially uniform thickness of dielectric material, since the thickness and material of the dielectric influences the morphology and failure profile of a wire. A particular wire width was selected based on the failure characteristics of a plurality of wires subjected to failure analysis. The SMM and method of the present invention allows such an analysis to be done with a single wire such as that shown in FIG. 5A scanned once or several times, since the electromigration effects can be imaged directly as they occur. As before, an excitation current source 27 provides an excitation current through the variable width CUT 70, which is coated with a dielectric material of substantially uniform thickness as expected in the final product (e.g., integrated circuit). The sensor 21 scans a row of data along the y-direction through a width of the CUT 70 and measures the magnetic field, then scans a different row of data through a different width of the CUT 70. These rows of magnetic field data are integrated into a two dimensional (2D) magnetic field map, which is converted to a current density image that graphically represents the morphological change due to electromigration within the CUT 70. This technique may be more practical for measuring the effect of wire width on the electromigration of a wire since most ICs have wires of different widths, but the technique is equally valid for measuring electromigration through any cross sectional area of the wire.

Figure 5B:
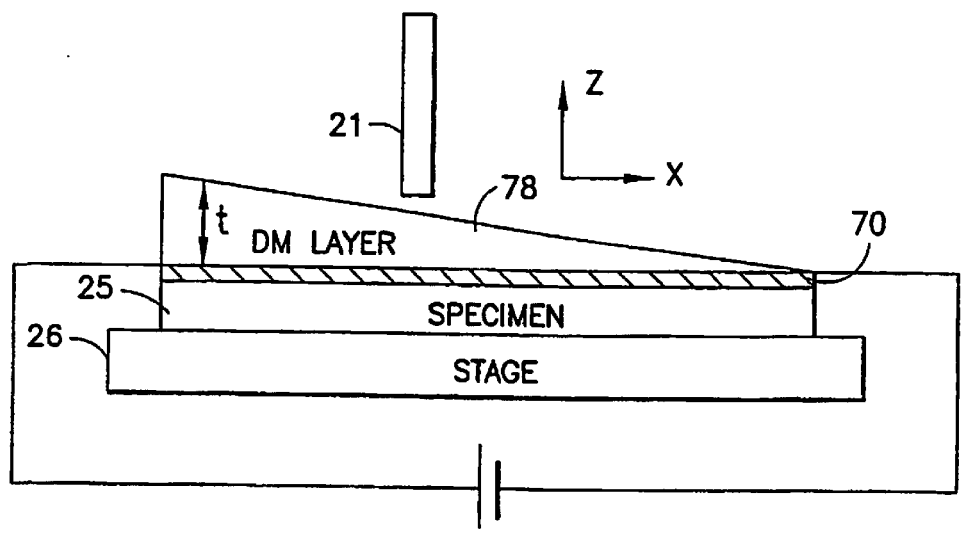
FIG. 5B is a simplified block diagram showing a dielectric material of variable thickness t under test.

Similarly, FIG. 5B depicts in profile view (i.e., x-z plane) testing of a wire 70 defining a substantially uniform width that is covered by a dielectric material (DM) 78. The DM 78 defines a variable thickness t. Scanning of the wire 70 is similar to that described with reference to FIG. 5A, so that a scan of one row yields magnetic data for a first thickness of the DM layer 78 and a scan of a different row yields magnetic data for a different thickness of the DM layer 78. This geometry (i.e., variable thickness of the DM layer 78) can be used to study the effect of overlayer thickness on electromigration. Prior art techniques match a layer thickness of dielectric material to a wire by coating a plurality of substantially equivalent wires with varying layer thicknesses of a single type of dielectric material, and testing each wire until failure. By measuring the evolution of morphological change in the CUT 70 using the SMM 20, an optimal thickness that most efficiently suppresses the electromigration can be easily selected for any particular dielectric material.

Figure 5C:
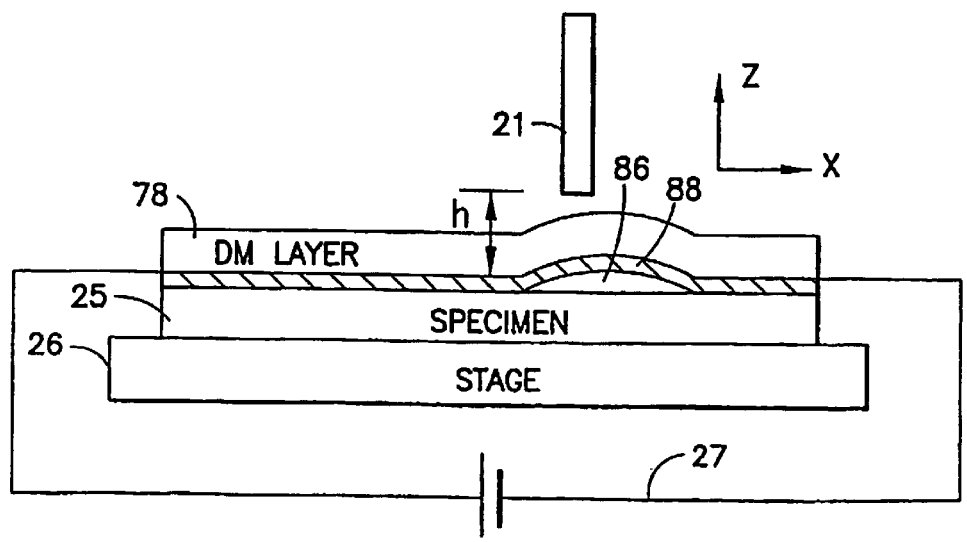
FIG. 5C is a simplified block diagram showing a conductor that has delaminated from a substrate without breaching a dielectric layer under test.

It is also useful to determine the potential deformation of the CUT 70, which can occur under stressing conditions of high temperature or high excitation current. The present invention may be used to sense an area of delamination 88 as depicted in FIG. 5C, wherein the CUT 70 has separated form an underlying substrate 86. A sensor 21 affixed to a mount 28 is scanned over a specimen 25. The specimen comprises a substrate 86 such as silicon upon which a conductor CUT 70 is mounted, with or without a layer of dielectric material 78 overlying the entire structure. A source of excitation current 27 supplies power to the CUT 70 and the sensor 21 scans the associated magnetic field as previously described. Where the excitation current is a stressing current, the sensor 21 may be scanned in a non-contact mode for thermal protection of the sensor 21, wherein the sensor is preferably thermally coupled to a heat sink. In that instance, the sensor would scan in non-contact mode while maintaining a constant distance h between the sensor and the CUT 70. If there is delamination 88, the magnetic field map and the resulting current density image will readily reveal the delaminated portion 88 in contradistinction to the normal (non-delaminated) portion. A SMM 20 may be used as an investigative tool for an IC or conductor that has already failed. Knowing the width of the CUT 70 allows the depth to be calculated using peak-to-peak data spacing $d_{ptp}$ as in the equation below. The sensor 21 is used to measure magnetic field peaks associated with different portions of the CUT 70. The disparity in depth is readily determined, and is used to indicate delamination even though the dielectric layer remains compliant (i.e., not breached or ruptured).

Figure 6A:
FIG. 6A is the physical mask template of a notched wire.
Figure 6B:
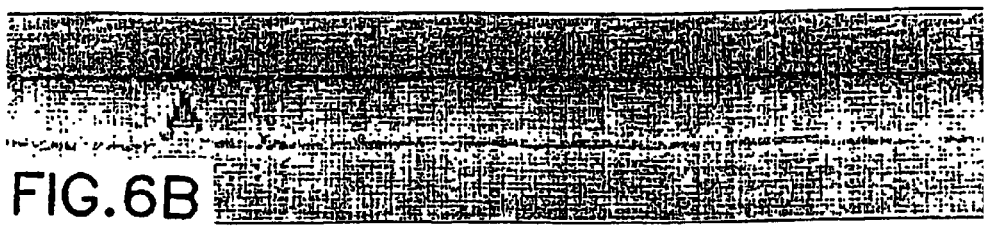
FIG. 6B represents the raw two dimensional magnetic field map.

As an example of the resolving power and real-time capabilities of this invention, numerous current-carrying wires with different geometries were initially patterned and scanned. The shape of one such wire, 67, which contains a triangular notch, is shown in FIG. 6A. The wire 67 was scanned while carrying a 2 mA modulation current at a frequency of 80 kHz, yielding the raw 2D magnetic field map shown in FIG. 6B.

Figure 6C:
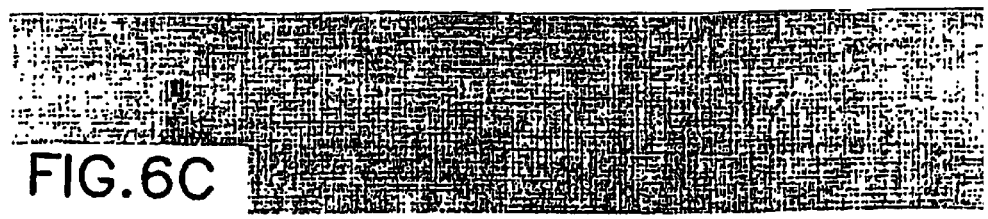
FIG. 6C is the converted current density image from the two dimensional magnetic field map of FIG. 6B.

The out-of-plane (e.g., z component) magnetic field data sensed by the sensor 21 is converted to an in-plane (e.g., x and/or y components) current distribution. As referred to herein, in-plane refers to a plane parallel to the surface 64 of the specimen 25 that is adjacent to the sensor 21. It can be shown that both in-plane components of the current density are determined absolutely with knowledge of any one component of magnetic field. The effective sensor height h, which is an important parameter for this transform, is calculated by comparison of experimental and analytical results for a current-carrying wire of known dimensions (such as a reference wire 72). Applying algorithms that convert magnetic fields to current densities yields both in-plane (x, y) components of the current density. FIG. 6C is the converted current density image from the raw magnetic field map of FIG. 6B, and shows the calculated horizontal component of the current density flowing through the notched wire 67 shown in FIG. 6A. Because total current flowing through the wire 67 is known, these data can be easily normalized to provide actual current density values without calibration of the magnetic sensor. Alternatively, a test sample with known parameters may be scanned and the data used in an inverse fashion to determine the field sensitivity of the magnetic sensor. No optimization of data or smoothing algorithm has been used in obtaining the image of FIG. 6C. FIG. 6C also shows directly the current crowding that occurs at the notch.

Images such as FIG. 6C show that current density may be used to represent the shape of a wire, and more than one such image can show how that shape changes over time due to electromigration effects by measuring current density for at least two points in time. The sensor 21 used for such imaging may be a MTJ, a GMR, or a Hall effect (ordinary or extraordinary) sensor, depending upon the particular application. Typically, MTJ's and GMR's are appropriate for high temperature testing, with MTJs being preferred for their better field sensitivity. When correcting for thermal drift, the reference conductor 72 should be within a distance of the CUT whereby the expected change in resistance due to thermal drift should be negligible compared to the desired system resolution. When a plurality of images are displayed relative to one another in time, a 'movie' of electromigration within the CUT 72 may be assembled.

Temperature may be controlled at the sensor, and speed of data collection may be enhanced, by swapping the sensor between scanning in a contact mode (e.g., scanner in contact with a surface of the specimen) and a non-contact mode (e.g., scanner not in contact with the surface, preferably <1–2 micron spacing). At the times when a high stressing current is imposed through the CUT 72, the sensor may be scanned in the non-contact mode and effectively cooled by a heat sink as described above. Resolution is less refined using a non-contact scan, but resolution need not be maximized while the CUT 70 is subjected to the stressing current. In addition, this allows for a larger pixel size, which correspondingly increases system speed, for time-critical applications. Once a defect is detected at the lower resolution, the stressing current may be reduced to an excitation current and the specimen then cooled to a temperature that will not damage the sensor. The sensor may then scan the specimen in the contact mode for better resolution of the defect first detected under higher temperature and lower non-contact scan resolution. Preferably, the non-contact mode scans the sensor at a much greater speed than the contact mode, since resolution is diminished and the electromigration effects are not yet of dominant interest when in the non-contact mode. The transition from the non-contact mode to the contact mode, and vice versa, may be made based on a minimal field amplitude fluctuation from the initial state, by a minimal change in sample electrical resistance, or by a minimal change in the proximity of the data peaks in the CUT 70, indicating a change in morphology, or by a combination of the three. The sensor 21 may scan, in the non-contact mode, a predetermined path that follows a known theoretical profile of a known and undamaged conductor. In general, when the sensed magnetic field deviates sufficiently from the theoretical profile, the sensor can be scanned in the contact mode to resolve more detail within the CUT 70.

Generally, when accumulating data from scanning the sensor 21 over the CUT 70, data spikes are removed (they are due to sensor hysteresis) and low-frequency data drift is filtered out by subtracting the mean value for each row of data from the overall data. The data rows are aligned to compensate for thermal drift as discussed above. In the case of non-constant current measurement, current fluctuations are corrected for by dividing each row of data by the measured current at the time data for that row was gathered. The magnetic field data are converted to current density data and made into images, all images are colored for current density or otherwise distinguished, each image is converted to a bitmap or a TIFF image, and the images are assembled into a 'movie' that depicts the time evolution of electromigration. If required, the current density across each row of data can be normalized to a single value by virtue of the continuity equation.

In certain instances such as elevated temperatures, the pinning layer of the sensor may become unpinned, causing non-uniformity in the direction of the magnetization. In this instance, the performance of the sensor may be deteriorated. Rather than replacing the entire sensor itself, a repinning process can be activated automatically by software and hardware that checks the sensor 21 response and runs the repining process if sensor response 21 drops below a predetermined threshold. The repinning process can be accomplished by subjecting the sensor to an external magnetic field pulse, whose direction is parallel to the pinning direction. In the case of magnetoresistive sensors, a current pulse of predetermined width and intensity can be applied to the sensor film itself and used to re-pin the element (this is termed a "reset pulse"). In the case of magnetic tunnel junction sensors, one can also deposit a thin film conductor in the vicinity of the sensor, and apply a DC pulse along the conductor in the appropriate direction. The magnetic field pulse resulting from the DC pulse should be large enough to reset the pinning layer. Such a thin film conductor may already be present in such devices for the purposes of sensor field biasing.

Figure 7A:
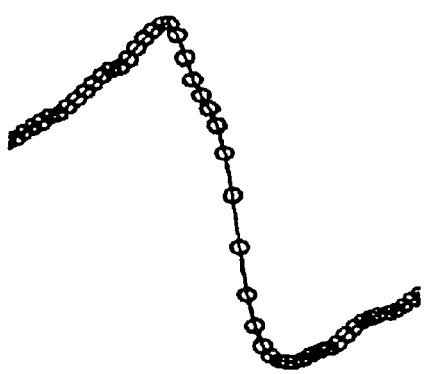
FIG. 7A is a magnetic field profile of a 0.4 micron wide conductor.
Figure 7B:
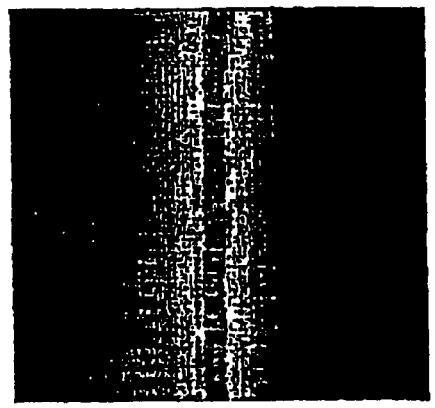
FIG. 7B is a current density image of the conductor of FIG. 7A.
Figure 7C:
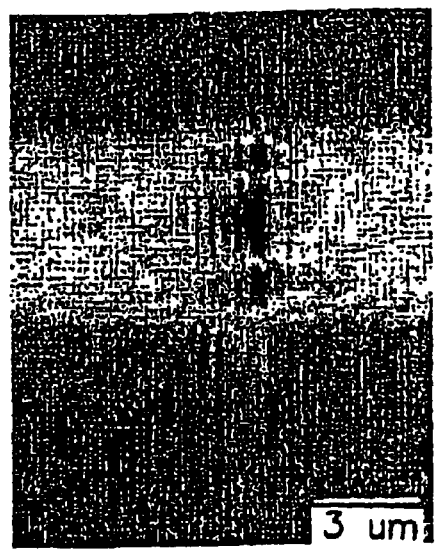
FIG. 7C is a current density image of an unpassivated 5 micron wide conductor with an electromigration-induced void.

FIG. 7A is a magnetic field profile of a 0.4 micron wide conductor, and FIG. 7B is a current density image of that same conductor. Both figures show that the area imaged has not undergone appreciable degradation due to electromigration. As a comparison, FIG. 7C is a close-up image of one void in an unpassivated 5-$\mu$m wide aluminum wire after undergoing an accelerated electromigration test under a current of $1.5 \times 10^6$ A/cm$^2$ for 4 hours. Such a stress caused a 7.5% increase in electrical resistance, and several physical voids were detected in the current density profile of the conductor. While not the same conductors, a comparison of FIGS. 7B and 7C show how effective the techniques presented herein can be in evaluating electromigration. The SMM 20 described above provides current density images at the sub-micron level that can be readily observed.

In another experiment, a heater and temperature controller were added to the SMM 20 to examine the time evolution of the current density distributions of wires damaged by electromigration. A series of images was obtained of two identical passivated aluminum conductors with lateral dimensions 400×3 μm² and a thickness of 0.2 μm. Each sample was deposited via evaporation and covered by a 0.1-μm-thick layer of $SiO_2$. The conductors, which have triangular metal reservoirs at each end, were subjected to conditions typical of an accelerated electromigration testing environment: a DC current density of $5.8 \times 10^6$ A/cm² was applied at an ambient temperature of 160 C. The samples were thermally annealed for several hours at 180 C before the initial application of current to separate thermal and electromigration effects. For each measurement, the sample was cooled, scanned using the microscope, and the process repeated until the sample failed. The two samples showed strikingly similar void morphologies as electromigration took place. Each showed void formation occurring in two primary areas: in a small (~15 μm) region of the cathode reservoir, which was the failure site of both samples, and in a longer (~60–100 μm) section of the conductor near the anode. As a check, the current polarity was reversed for one sample, and the void morphology also reversed. Images of cathode voiding taken from sample A are presented in FIGS. 8A–E and images of the anode region from sample B are presented in FIGS. 9A–D, although each sample showed qualitatively similar behavior in each region. The specimen resistance was monitored and used to automatically stop the electromigration process each time the sample resistance increased by an additional one percent.

Figure 8A:
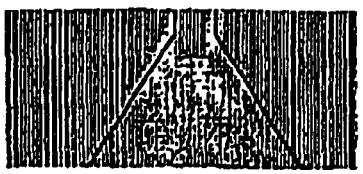
FIGS. 8A–D are images showing the time evolved current density flowing through the cathode of an passivated 3 micron wide conductor undergoing electromigration.
Figure 8B:
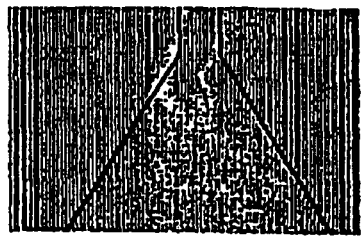
Figure 8C:
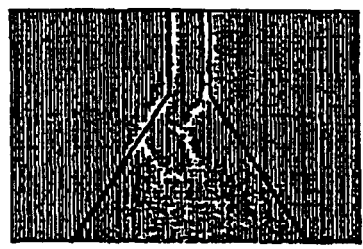
Figure 8D:
Figure 8E:
FIG. 8E is a post-mortem SEM micrograph of the sample of FIGS. 8A–D confirming the failure mechanism.
Figure 9A:
FIGS. 9A–C is a time lapsed series of current density images showing void dynamics near the anode of a 3 $\mu$m conductor undergoing electromigration.
Figure 9B:
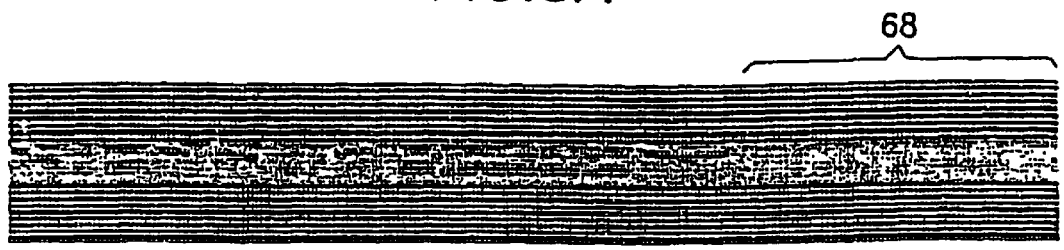
Figure 9C:
Figure 9D:
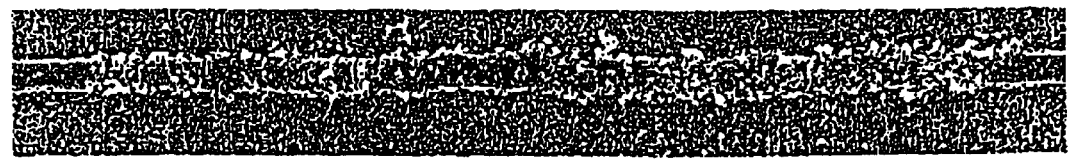
FIG. 9D is an SEM micrograph of a region of a conductor similar to that of FIGS. 9A–C that makes more apparent the voiding process.

A series of current density images at the cathode of sample A are shown in FIGS. 8A–D. These images depict the evolution of current flow at four stages of accelerated testing, each separated by roughly 3–5 hours. FIG. 8E is a post-mortem scanning-electron-micrograph confirming the failure mechanism. It can be seen that voiding at the cathode nucleates at both edges of the sample at different times, and later a void is seen to nucleate in the center of the cathode. It appears that voiding has already begun at the lower edge of the sample in the first current density image (FIG. 5A), which was taken 5.7 hours after the beginning of the test, indicating that there was little or no incubation time before void formation began. This failure location, which is at a site of large flux divergence, is expected from basic theoretical arguments For sample B, the process was slightly different: rather than scanning the sample at regular time intervals, the sample was instead scanned with each 1% increase in resistance. A zoomed-in view of the current density near the anode of sample B is shown in FIGS. 9A–C. A large number of voids are observed near the anode, which is located just off the left side of the images of FIGS. 9A–C. The area of the conductor to the right of the center of the images of FIG. 9A–C, generally indicated by reference number 68 represents a section of the conductor still undamaged and therefore having a relatively constant current density; the remainder of the conductor, save the cathode, has this same undamaged profile. It can be seen that nearly all the voids appear to nucleate at the top and bottom edges of the conductor. This is expected for electromigration tests in the high-current regime due to the large thermal gradients occurring at the conductor edges in this regime. In contrast to this, the tests conducted on the unpassivated aluminum conductor revealed a number of voids (one of which is shown in FIG. 7C nucleated in the center of the conductor). In addition, the voids in the unpassivated conductor were more randomly dispersed throughout the conductor, which is also expected for samples with lower current densities.

The sample resistance took fourteen hours to increase by 1% initially, but then began to increase much more rapidly, and the next two 1%-increments took only an additional 0.3 and 0.9 hours, respectively. The current density profiles of the same section of the conductor near the anode after each of these intervals are shown in FIG. 9. The current profiles are similar and show many of the same features, but there are some notable changes. First of all, the voided area is gradually moving towards the cathode, as can be seen from the motion of the right-most voided areas to the right. From these images, we can estimate the drift-velocity of the vacancies to be 4.5±0.5 μm/hour. Secondly, the void morphology has changed a great deal in the 1.2 hours between the first and last image: near the center of the image, it can be seen that the red "hot spots", which indicate where the majority of the current is flowing, have changed as the current alters its path. In the first image, it flows along the top of the conductor for a relatively long distance of ~18 microns, while in the second image it flows along the bottom of the film for a longer distance, before "detouring" to flow along the top, and by the third image, it only flows along the top of the conductor for the last five microns of voided area. A scanning electron micrograph of the anode region of sample A is shown at the bottom of FIG. 9. The similarity in the morphology between the two samples is readily apparent.

This SMM technique can observe dynamics unavailable to traditional microscopy techniques. Magnetic imaging may reveal areas where current density appears greater in one scan as opposed to another scan. These areas may be indicative of the existence of voids that have not grown completely through the thickness of the wire, or these areas could indicate regions where metal has accumulated, creating a wider path for the current and increasing the local current density at the expense of other areas. Another way to look at this is as follows: if it is assumed that the current will distribute itself evenly over the available cross-sectional area of the wire at each horizontal distance, these images can be thought of as representing the relative thickness of the wire across each vertical cross-section of the wire. This observation is the key to understanding the current fluctuations as a direct representation of morphology. The presently preferred embodiment does not directly determine the overall normalization constant; therefore, an observed region of uniform current flow indicates that the wire thickness is constant, but not the actual value of the thickness itself. Any uncertainty may be resolved by the application of more traditional microscopy techniques to these samples. For the purposes of this invention, it is assumed that this morphology is indeed created by voiding, and not accumulation.

Figure 10:
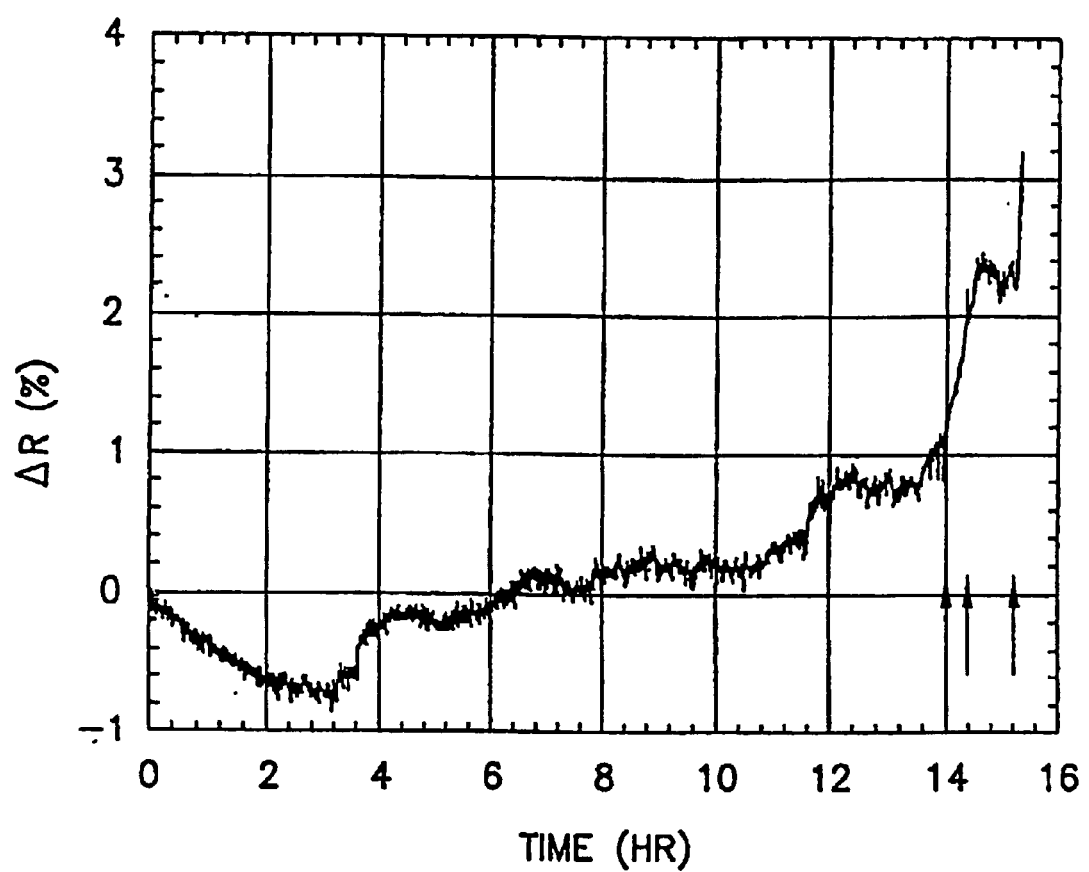
FIG. 10 is a graph of resistance as a function of time for one electromigration experiment.

Resistance is plotted as a function of time in FIG. 10 for a specimen subjected to stressing currents. Though not reproduced here, this same kind of morphology involving edge-nucleated voids and an alternating current path was also seen in sample A.

Further in accordance with this invention, the control of the height of the sensor 21 from the surface 64 of the specimen 25 may be automated to measure the evolution of electromigration under stress. For example, a specimen 25, such as a wire or IC, may be mounted on the SMM 20 and subjected to a stressing temperature $T_{stress}$ or current $i_{stress}$ for a duration of time that is above the typical operating temperature $T_{op}$ or current $i_{op}$. During this time, the sensor 21 is held at some distance above the surface 64 of the specimen 25. The resistance of the specimen may be measured to determine the onset of electromigration. The specimen 25 is then cooled to $T_{op}$, and scanned with the sensor 21 in a contact mode to generate images of the current density and void morphology at that time based on the sensed magnetic fields. The above cycle can be repeated until the specimen 25 fails. The series of data gathered by the sensor 21 can then be animated to give a graphical view of void formation and propagation.

If the electromigration experiment is done subsequently with the magnetic scans, there are several criteria that can be used to determine when to discontinue the application of current and begin a scan. Three such criteria are as follows. The simplest is to end the experiment after a fixed amount of time (typically several hours) has passed. The second criterion is to end the experiment after a certain total change ill resistance (typically 0.5–1%) is observed. The final criterion is to end the experiment when a certain resistance derivative (slope) is obtained. This final condition is particularly useful for ending the current flow before the wire experiences total failure. The use of these criteria are highly dependent on the system being studied; for example, in a copper interconnect the resistance change is likely to be much more significant and total failure of the system is not as likely.

The above describes the design and operation of the SMM 20 when used for sub-micron current imaging applications. Directly imaging voiding that is induced by electromigration occurring in aluminum and other types of wires is one important application. Time-evolution of voiding that leads to wire failure, and the determination of drift velocity further add to the value of the SMM 20 disclosed herein.

Figure 11:
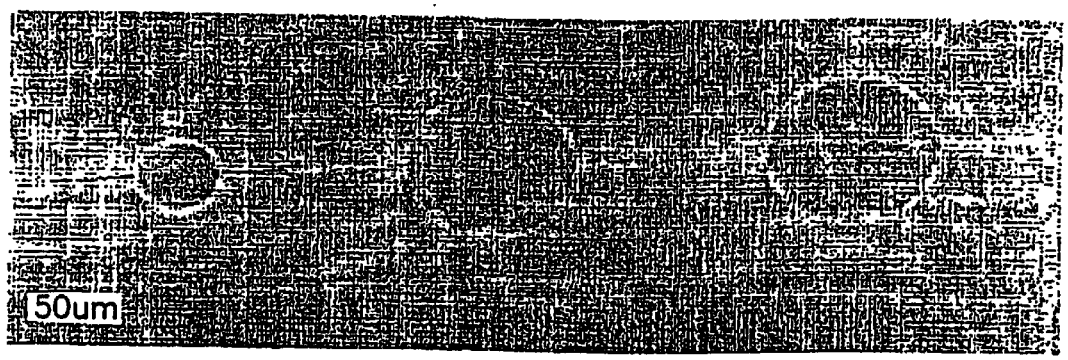
FIG. 11 is the converted current density image in a series of patterned rings.

The SMM 20 is capable of obtaining current density images of complicated geometries. As an example, FIG. 11 shows the converted current density image from a series of patterned rings. One can study morphological changes in complicated geometries.

The choice of a magnetic sensing technology is important because the technique relies on the use of a magnetic sensor that satisfies the noise, sensitivity, spatial resolution, and ambient operating condition requirements imposed by current state-of-the-art electromigration testing methods. Two presently preferred sensors for die SMM 20 for studying EM operate under ambient non-cryogenic conditions and over a wide frequency range.

The first type of sensor is the giant magnetoresistance sensor (GMR). These devices, which are widely used in the magnetic data storage industry, offer excellent spatial resolution and adequate sensitivity.

The second type of sensor is based on a magnetic tunnel junction (MTJ) sensor. These sensors offer excellent sensitivity and can be used to achieve very high spatial resolution and high frequency response. A SMM 20 according to the present invention may use either a GMR or a MTJ sensor. Either is suitable for real-time electromigration imaging, but MTJ sensors are presently the most preferred.

The SMM 20 may be optimized for magnetic field sensitivity and noise for substantially real-time operation. One of the most desirable features of this technique is that it is conducted in real-time; that is, that the SMM 20 collects data with sufficient speed to allow for the creation of time-evolved current density profiles as EM failure testing takes place.

In order to achieve this goal, the speed of operation of the SMM 20 for real-time imaging is maximized. Because the speed is intrinsically related to the system sensitivity, noise, and resolution, there are several issues involved in the optimization of the system speed. First, the sensing element (s) 21 is optimized for maximal signal-to-noise ratio and for frequency response. Second, the intrinsic sensor noise, as well as the noise of the surrounding electronics, is minimized.

In certain instances, the magnetic sensor 21 is brought close to or in contact with the surface 64 of the specimen 25 in order to provide sub-micron spatial resolution of the magnetic fields at the surface. This exposes the sensor 21 itself to elevated temperatures, which imposes additional requirements on the sensing element. There are potential problems accompanying use in a high-temperature environment. Of these, the most obvious is the potential magnetic de-pinning of the magnetic sensor 21. This invention, in one aspect, provides a sensor 21 that is resistant to high temperatures by an optimization of materials and fabrication parameters, described below.

Improved sensitivity of the MTJ sensor 21 facilitates both the resolution and the depth of acquisition requirements for ICs. The SMM 20 is enabled to extract depth information, which is one of the great advantages of the SMM 20. Based on electromagnetism theory, conducting wires at different depths generate differing depth-sensitive magnetic field profiles. Analysis of these profiles allows the SMM 20 to "see" and distinguish between electromigration dynamics occurring in different layers. Specific software de-convolution algorithms are used for this purpose, described below.

Figure 12:
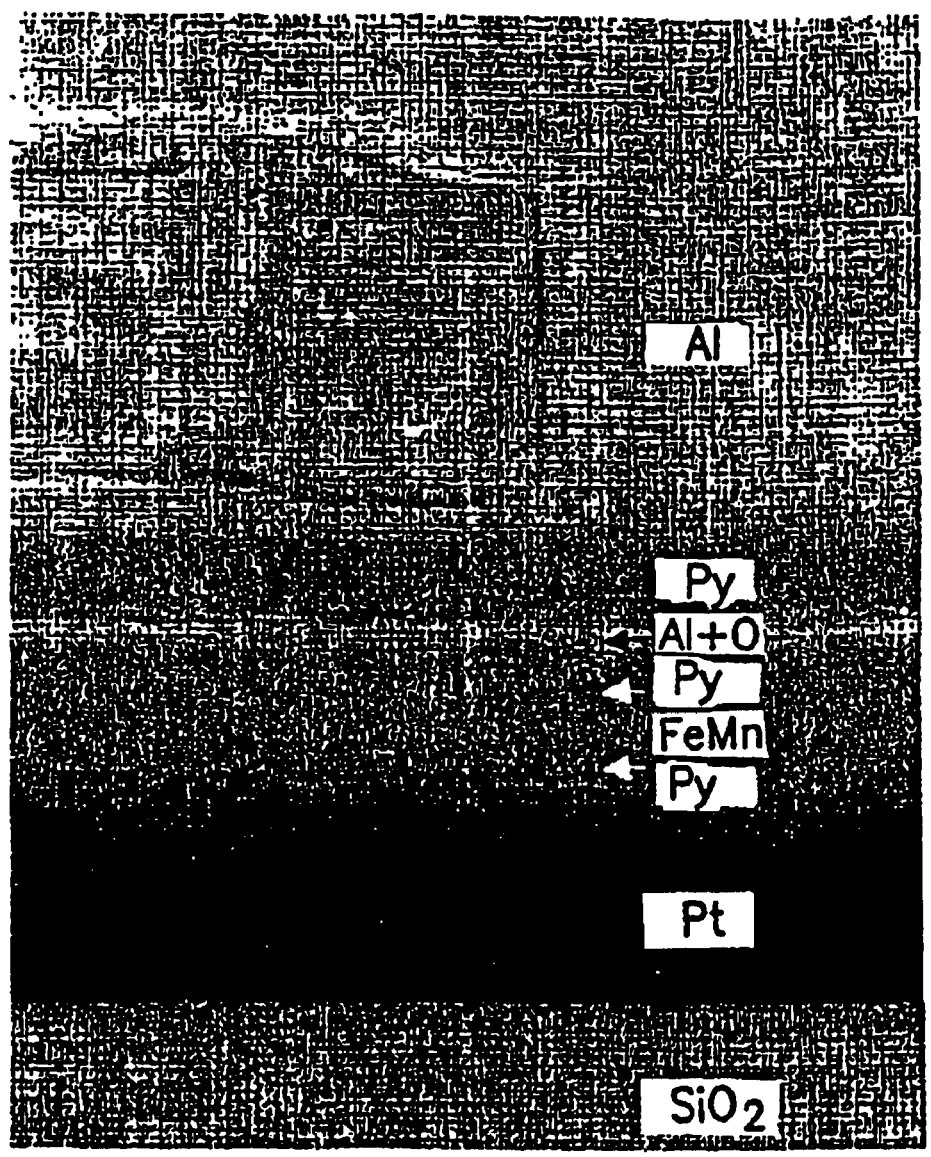
FIG. 12 is a cross-sectional TEM image of a patterned magnetic tunnel junction.
Figure 13:
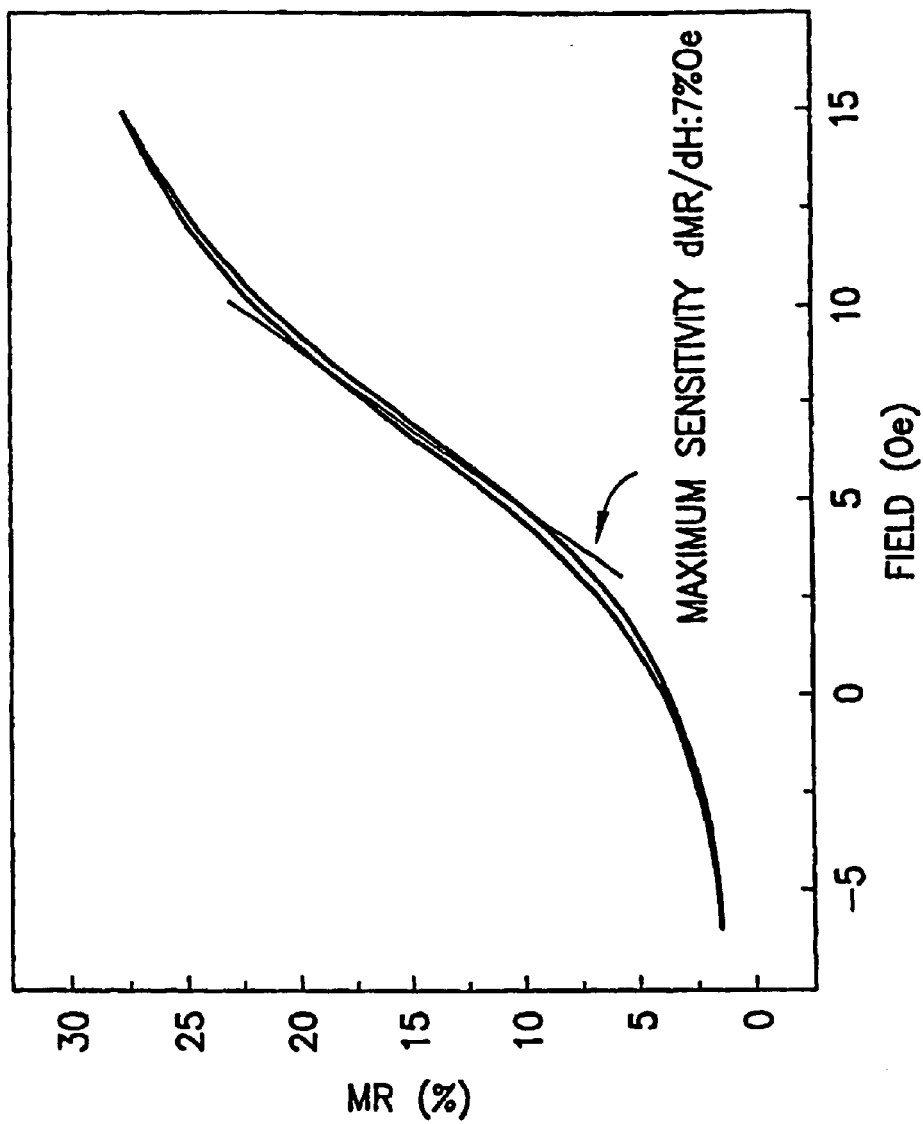
FIG. 13 is a transfer curve of a typical magnetic tunnel junction sensor, with an MR>30%, a maximum sensitivity of 7% MR change per Oe, and little hysteresis.

The fabrication of the MTJ sensor element will now be discussed. In one arrangement, a self-aligned optical lithographic process is used to pattern the MTJ films to sizes down to a few microns. To accomplish submicron resolution, electron-beam lithography is preferably used to obtain very small sensors. FIG. 12 shows a transmission electron micrograph of an MTJ layer structure. A 2-inch Si wafer typically contains hundreds of MTJs having varying shape, aspect ratio, and area. After patterning, junction properties are characterized by measuring tunneling resistance R and MR ratio in an applied magnetic field up to 200 Oe. In practice, MTJ sensors 21 have been produced and characterized with high sensitivity (7%/Oe) and a very linear transfer curve, as shown in FIG. 13. Because it has been demonstrated that an applied hard-axis (perpendicular to the sensing direction) bias field has a critical impact on the noise and linearity properties of MTJ sensors, the transport system has a built-in hard-axis capability up to 200 Oe. With this system, the transport properties of sensors can be investigated accurately and quickly.

The sensitivity of a MR field sensor 21 depends not only on the maximum MR ratio, but also on the inherent electronic and magnetic noise. Using sensors 21 prepared by the process described above, sensor noise as a function of frequency is measured to determine the ultimate field sensitivity.

Figure 14:
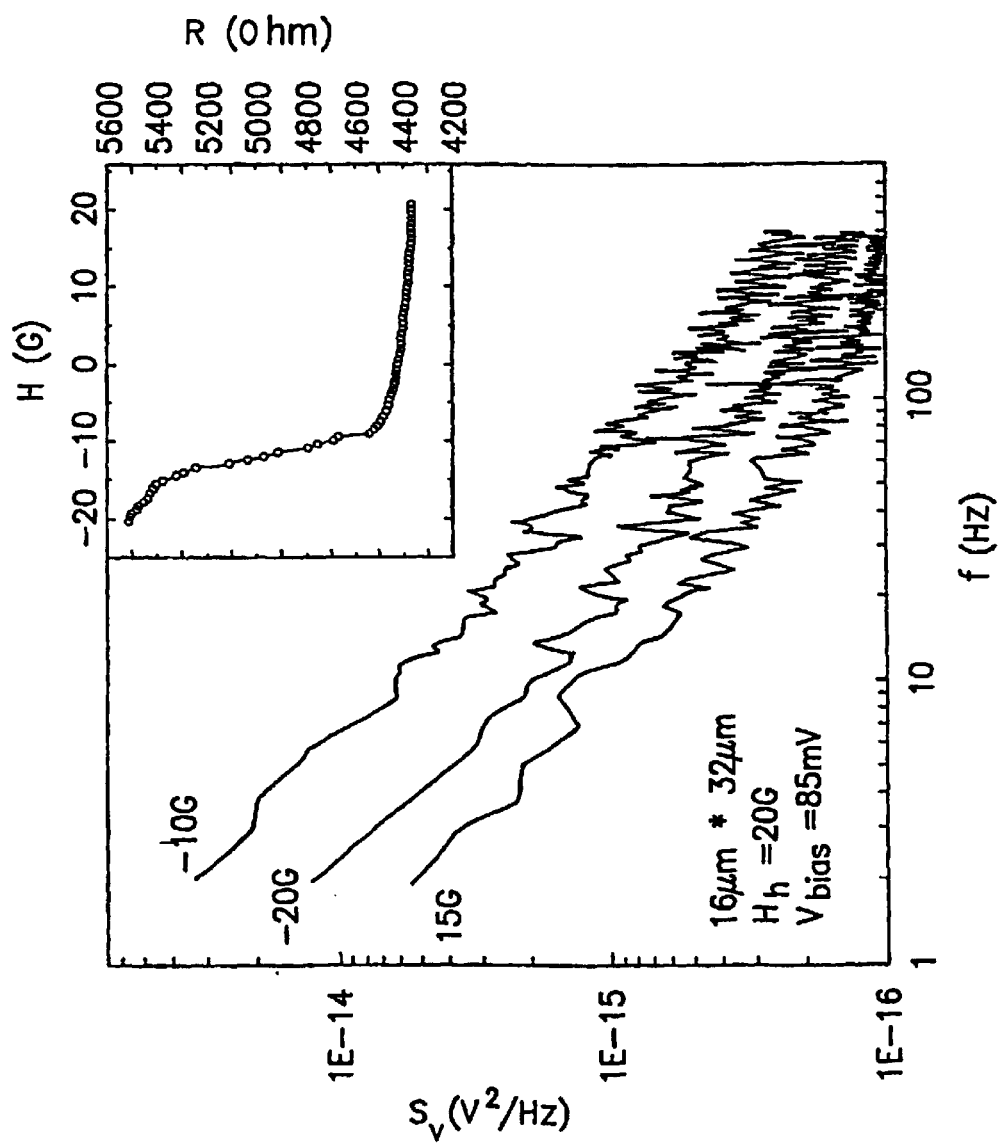
FIG. 14 is a graph of voltage noise power versus frequency at different biasing fields for a magnetic tunnel junction sensor element. The inset shows resistance versus magnetic field for the same sample.

Field-sensing noise in MTJ sensors 21 is reduced through various means. In the MTJ sensor 21, with a linear field response, the field noise power $S_H(f)$ to be measured is dependent on the voltage noise power $S_V(f)$, $$S_H(f) = \left(\frac{1}{R}\frac{dR}{dH}\right)^{-2}\left(\frac{1}{V}\right)^2 S_V(f), \tag{1}$$

$$S_V(f) = 4kRT + 2eVR + \alpha\frac{V^2}{Nf^\gamma}. \tag{2}$$

where e is the electron charge, k is Boltzmann's constant, $\alpha$ and N are specimen-dependant parameters, and $\gamma$ ranges between 0.6 and 1.4. The three terms in $S_V(f)$ are called Johnson, shot, and 1/f noise, respectively. In general, a large slope of MR, $$\frac{1}{R}\frac{dR}{dH},$$

tends to reduce the field noise, making the large saturation value of MR in MTJ sensors a considerable advantage for sensor applications. Reduction is needed in the saturation field required to rotate the magnetization of the free electrode layer 60, 62 from equilibrium ($\theta_1=0$) to saturation ($\theta_2=90°$). For this purpose a free electrode layer 60, 62 uses a permalloy (Py=$Ni_{81}Fe_{19}$) thin film 62 patterned into a shape optimized to minimize the saturation field while maintaining integrity of the magnetic domain. Other magnetically soft metals with zero magnetostriction and high spin polarization can also be used. At high frequency (e.g. above 500 Hz), the field noise is dominated by the field-independent Johnson and shot noise. At frequency ranges below this figure, the 1/f noise is the dominating factor. FIG. 14 is a graph of voltage noise power versus frequency at different biasing fields for a magnetic tunnel junction sensor element made by us. The inset shows magnetic induction versus resistance for the same sample.

Because the SMM 20 can be operated at a relatively low frequency (note, however, that the MTJ sensors 21 are capable of operating at 5 GHz), 1/f noise is the greater concern. This noise can originate from many sources, such as disorders (potential and magnetic trappings) and thermal fluctuation of magnetization in the electrodes 54, 56 and 60, 62.

There are several preferred methods to further improve sensor 21 performance. First, thermal annealing reduces 1/f noise. This enhancement is possibly due to the reduction of disorders near the interface, which may also reduce the 1/f noise. Second, the thin (1 nm) Co film 60 adjacent to the tunnel barrier 58, followed by a thicker (10 nm) permalloy film 62, provides advantages. The Co ferromagnet ($T_c$=1446 K) has a larger spin-wave stiffness constant than permalloy ($T_c$=850 K). Therefore, the thermal fluctuation of magnetization ($\Delta M$) is much weaker in Co than in permalloy. Since tunneling occurs near the interface, the associated 1/f noise due to $\Delta M$ will be reduced. Co also has a larger spin polarization, which improves the MR ratio. Furthermore, since the free layer's overall magnetization is dominated by the permalloy film 62, the free electrode layer 60, 62 retains the magnetic softness that is important to sensor 21 operation.

Sensors 21 may also be fabricated and tested for operating at high-temperatures, since electromigration imaging typically is preferably conducted at a temperature of about 170° C. and higher. There are several techniques used to Make sensors 21 operable at such high temperatures. First, the pinning layer in a MTJ sensor is dependent on the properties of the AFM layer, whose blocking temperature $T_{block}$ can range from 150–380° C., depending on the AFM material used. Above the blocking temperature, the pinning properties break down, which may cause the sensor 21 to fail. The blocking temperature increases from FeMn (160° C.), IrMn (270° C.), to PtMn (380° C.). As such, IrMn and PtMn materials are presently preferred for use in making a temperature resistant AFM layer 54. Second, as the sensor 21 must not be adversely affected by thermal diffusion, thermal diffusion may be controlled by automating the temperature control mechanism in the SMM, and/or incorporating of heat sinking mechanisms for the sensors 21. A continuous stream of air directed at the interface of the sensor 21 and the specimen 25 effectively dissipates heat that would otherwise accumulate within the sensor 21. The automated height control function, described above, that allows the sensor 21 to operate in a non-contact mode at a constant height above the surface 64 of the specimen 25 is also effective in isolating the sensor 21 from heated specimens 25 under accelerated EM environmental conditions. For example, a microscope 34, a camera, a laser aligned with a photoreceptor, or other such monitoring and measuring device, may be connected to a P.C. 50 that controls a servo motor 22A or piezoelectric motion stack that drives spacing between the sensor 21 and the surface 64 of the specimen 25 (i.e., z direction). The microscope 34 may be used to monitor a certain spacing between the sensor 21 and the surface 64 of the specimen 25. Variations are reported from the microscope 34 to the P.C. 50, which adjusts the servo motor 22A in a manner to re-acquire the spacing z. The use of one or more of the above methods enables sensor 21 to operate at temperatures equal to or greater than 170° C.

Real-Time Operation

Increasing the operating speed of the SMM 20 is also important for substantially real-time operation, which is enabled by optimizing the electronics built around the sensor 21. The Wheatstone bridge 40 coupled with the lock-in amplifier 43 for lock-in detection facilitates better measurements. The use of digital signal processing further improves real time performance. Speed and noise data for many different system configurations have been tested and compared to optimize the electronics. Because of the greatly improved sensitivity of the MTJ sensors 21 described herein, substantially real-time operation with high resolution is feasible using an MTJ sensor 21 with the above improved electronic set-up.

The peak-to-peak (PTP) spacing of the data, a parameter that can be measured very accurately, is given by $$d_{PTP}=\sqrt{4h^2+w^2},$$

where h is the effective sensor height (h) and w is the width of the current-carrying conductor 70. By controlling the values of h and w during patterning, this relation can be used to extract some important parameters about the system, for example, the intrinsic minimum sensor height z created by the mechanical profile of the sensing element 21. The above relation may also provide an additional capability for the disclosed SMM 20: given the size of the conductor 70, the depth of the flowing current may be calculated, or vice-versa, from the data. With the current resolution, d may be determined to within 0.05 $\mu$m, which means that for a 1 $\mu$m-wide wire buried under roughly 1 $\mu$m of insulator, one is able to determine the depth of the flowing current to within a few hundred Å. The most relevant application is to measure the width or depth of a buried wire using the SMM 20 to determine just how much thermal drift or electromigration has taken place. This feature can also determine which metal layer is active for currents flowing in multi-level integrated circuits.

Regarding the normalization of the current density: although most characteristics of the magnetic sensor 21, including its sensitivity, may not be known exactly, the current density may nevertheless still be normalized using a continuity equation, of which the equation for current J is shown below.

$$\frac{\partial}{\partial x}J_x + \frac{\partial}{\partial y}J_y + \frac{\partial}{\partial z}J_z = \frac{\partial \rho}{\partial t}$$

The above equation recites that current cannot be created or destroyed at a point. For example, assume that the specimen 25 is mounted such that current flows through an embedded wire in only the y direction. The sensor 21 scans along the x, y plane and gathers rows of data along the x axis and columns of data along the y axis. The total current across every row (i.e., spanning the wire perpendicular to the flow of current) is therefore equal to the instantaneous current passing through the specimen 25 at the time that row was measured. The instantaneous current can be measured precisely. An algorithm is applied to automatically normalize each row of data by applying a continuity equation, such as the above equation for current, to fix the total current density, which is in general known. The sensitivity of the sensor 21 can be determined by measuring the magnetic field profile of a known structure, e.g. an undamaged wire, at many different sensor heights (z), and fitting the resulting series of curves to the two unknown parameters: the effective sensor height h, and the sensor sensitivity. This is also the most accurate method to determine depth information.

While described above in the context of various materials, thicknesses, and other specific parameters, these are exemplary and not to be construed as imposing a limitation upon the practice of this invention. Thus, while described in the context of presently preferred embodiments, those skilled in the art should appreciate that various modifications of and alterations to the foregoing embodiments can be made, and that all such modifications and alterations remain within the scope of this invention. Examples herein are stipulated as illustrative and not exhaustive.

What is claimed is:

1. A method for measuring a change over time in morphology of a conductor-under-test (CUT) comprising:
    passing an excitation current through a conductor-under-test (CUT);
    measuring with a scanning magnetic sensor a first two dimensional (2D) magnetic field map associated with the CUT at a first time;
    measuring a second two dimensional (2D) magnetic field map associated with the CUT at a second time; and
    converting the first magnetic field map to a first current density image and the second magnetic field map to a second current density image, each image representing a morphology and current distribution of the CUT with sub-micron resolution.

2. The method of claim 1 wherein the sensor is selected from the group consisting of a magnetic tunneling junction (MTJ) sensor, a giant magnetoresistance (GMR) sensor, an extraordinary Hall effect (EHE) sensor, and an ordinary Hall effect (OHE) sensor.

3. The method of claim 1 further comprising correcting the measurement data obtained from the first and the second magnetic field maps for thermal drift of the CUT when the temperature of the CUT is greater than about 50 ĩC at any point.

4. The method of claim 3 wherein correcting for thermal drift comprises passing a reference current through a reference conductor without undergoing morphological change, measuring a 2D magnetic field reference map near the reference conductor, and aligning the first and second magnetic field maps relative to the magnetic field reference map.

5. The method of claim 4 wherein the reference current passing through the reference conductor is less than the excitation current passing through the CUT.

6. The method of claim 4 wherein the CUT is spaced from the reference conductor a distance greater than five times the width of the CUT but less than the effective temperature correlation distance.

7. The method of claim 4 wherein the CUT and the reference conductor are maintained at substantially the same temperature while measuring the first magnetic field map and the reference map.

8. The method of claim 1 further comprising displaying the first and second current density images relative to one another in a manner that shows a time evolution of the morphology of the CUT.

9. The method of claim 1 further comprising cooling the sensor with a heat sink while measuring at least one of the first or second magnetic field maps.

10. The method of claim 1 further comprising measuring a preliminary 2D magnetic field map with the scanning magnetic sensor spaced from a surface of a specimen in which the CUT is disposed, and wherein measuring the first and the second 2D magnetic field maps includes contact the sensor with the surface while so measuring.

11. The method of claim 10 wherein the specimen is raised to a stressing temperature $T_{stress}$ when the sensor is not in contact with the surface to avoid thermal degradation of the sensor, and then scanned at a lower temperature $T_{op}$ at defined intervals.

12. The method of claim 1 wherein the sensor comprises a giant magnetoresistance (GMR) sensor, the method further comprising subjecting the GMR sensor to a current pulse to re-pin the magnetic alignment of a pinned layer defined by the GMR sensor.

13. The method of claim 1 wherein the sensor comprises a magnetic tunnel junction (MTJ) sensor, the method further comprising subjecting the MTJ sensor to an external magnetic field pulse to re-pin the magnetic alignment of a pinned layer defined by the MTJ sensor.

14. A scanning magnetic microscope (SMM) comprising a magnetic field sensor, and further comprising:
    a first circuit for passing an excitation current through a conductor-under-test (CUT);
    a second circuit for passing a reference current through a reference conductor defining a known shape;
    a magnetic field sensor for obtaining a 2D magnetic field map generated by the CUT, said sensor capable of sub-micron resolution;
    means for moving said sensor relative to the CUT and the reference conductor;
    software for correcting a thermal drift of the CUT; and
    software for converting the 2D magnetic field map to current density image.

15. The SMM of claim 14 wherein the sensor includes an antiferromagnetic layer made from an alloy of PtMn, FeMn, or IrMn.

16. The SMM of claim 14 further comprising a heat sink.

17. The SMM of claim 16 wherein the heat sink is thermally coupled to the sensor, the heat sink comprising a stream of gas directed toward the sensor.

18. The SMM of claim 16 wherein the heat sink comprises a coldfinger that is thermally coupled to the sensor.

19. The SMM of claim 14 wherein a layer of dielectric material is disposed between the CUT and the sensor.

20. The SMM of claim 19 wherein the means for moving the sensor comprises moving the sensor into contact with a surface of the DM when a temperature of the DM is at $T_{op}$, and moving the sensor out of contact with the surface when the temperature of the DM is greater than $T_{op}$, where $T_{op}$ is a predetermined safe operating temperature.

21. The SMM of claim 19 wherein the means for moving the sensor relative to the CUT comprises means for moving the sensor at a first speed when the sensor is spaced from the CUT a distance $z_1$ for measuring a magnetic field map with a first resolution, and means for moving the sensor at a second speed when the sensor is spaced from the CUT a distance $z_2$ for measuring a magnetic field map with a second resolution.

22. The SMM of claim 21 further comprising means to automatically move the sensor from the second speed to the first speed when the sensor detects an occurrence of electromigration in the CUT, wherein $z_2>z_1$.

23. The SMM of claim 14 wherein the sensor is selected from the group consisting of a magnetic tunneling junction (MTJ) sensor, a giant magnetoresistance (GMR) sensor, an extraordinary Hall effect (EHE) sensor, and an ordinary Hall effect (OHE) sensor.

24. The SMM of claim 14 wherein the reference current is less than the excitation current, via either separate current sources or differing resistances.

25. The SMM of claim 24 further comprising a first power supply that supplies current to the first circuit and a second power supply that supplies current to the second circuit.

26. The SMM of claim 14 further comprising software for converting a time-lapsed series of sensed 2D magnetic field maps associated with the CUT to a series of time lapsed images of current density that represent a time-lapsed change in a morphology of the CUT.

27. A method for determining a width (w) of a conductor-under-test (CUT) disposed under a dielectric material, comprising:
  determining the depth of the CUT from a surface of an overlying layer of dielectric material;
  passing an electrical current through the CUT;
  measuring a magnetic field associated with the electrical current in the CUT with the magnetic sensor at a height (h) of the sensor above the CUT;
  measuring a peak-to-peak spacing ($d_{PTP}$) of the magnetic field spatial profile across a width of the CUT; and
  determining the width using a relation that is mathematically equivalent to $d_{PTP}=\sqrt{4h^2+w^2}$.

28. A method for determining a normalized electrical current density in a wire disposed beneath a surface of a specimen, comprising:
  disposing a surface of a specimen adjacent to a scanning magnetic sensor;
  passing an excitation current through a wire disposed beneath the surface;
  measuring a first two dimensional magnetic field map with the scanning magnetic sensor at a height $z_1$ above the surface;
  measuring a second two dimensional magnetic field map with the scanning magnetic sensor at a height $z_2$ above the surface, wherein $z_2>z_1>0$;
  converting the first and second magnetic field maps into a first and second current density images; and
  normalizing the first and second current density images by employing an electromagnetic continuity equation.

29. A method for representing an evolution over time of electromigration within a conductor-under-test (CUT) comprising:
  passing a reference current through a reference conductor;
  passing an excitation current through a CUT at a first time and at a second time;
  measuring, with a scanning magnetic sensor, a first sensed 2D magnetic field map associated with the CUT at the first time;
  measuring, with a scanning magnetic sensor, a second sensed magnetic field map associated with the CUT at the second time;
  aligning each of the first and the second sensed magnetic field maps relative to the reference conductor;
  converting the first and second sensed 2D magnetic field maps to a first and a second current density images; and
  displaying the first and second current density images in sequence.

30. The method of claim 29 further comprising correcting for sensor hysteresis by removing spikes of data from the sensed magnetic fields or by automatically reacquiring rows of data upon the automated detection of spikes with a pre-determined magnitude.

31. A method of measuring electromigration as a function of a cross sectional area of a wire comprising:
  providing a wire that defines a first cross sectional area and a second cross sectional area that differs from the first;
  providing a dielectric material that defines a substantially uniform thickness over the wire;
  passing an excitation current through the wire;
  measuring a first 2D magnetic field map associated with the wire first cross sectional area and a second 2D magnetic field map associated with the wire second cross sectional area;
  converting the first 2D magnetic field map to a first current density image and the second magnetic field map to a second current density image, each image representing electromigration effects in the wire.

32. A method of measuring electromigration as a function of a thickness of a dielectric material overlying a wire comprising:
  providing a wire that defines a substantially uniform thickness;
  providing a dielectric material defining a first thickness over a first portion of the wire and a second thickness over a second portion of the wire;
  passing an excitation current through the wire;
  measuring a first 2D magnetic field map associated with the first portion of the wire and a second 2D magnetic field map associated with the second portion of the wire; and
  determining whether electromigration induced morphology has occurred at the first portion or at the second portion of the wire.

33. The method of claim 32 wherein the dielectric material defines a continuously variable thickness over the length of a CUT.

34. A method for determining whether an electrical conductor has delaminated from a substrate, comprising:
  providing a substrate and a conductor;
  passing an electrical current through the conductor;
  measuring at a first time, with a scanning magnetic sensor having sub-micron resolution, a first 2D magnetic field map associated with the conductor being bonded to the substrate;
  measuring at a second time, with the scanning sensor, a second 2D magnetic field map associated with the conductor;
  converting the first and second 2D magnetic field maps to a first and second current density images; and
  comparing the first and second current density images using depth-detection methods to determine whether the conductor has delaminated from the substrate.

35. A method for measuring a change over time in morphology of a conductor under test (CUT), comprising:

applying a stressing condition to the CUT;

passing an excitation current through the CUT;

measuring a first and a second two dimensional magnetic field map associated with the CUT at a first and second time, respectively;

converting the first and second magnetic field maps to a first and a second current density image, respectively, wherein each image represents morphology and current distribution in the CUT.

36. The method of claim 35 wherein the stressing condition comprises at least one of the following: electrical current through the CUT; raising a temperature of the CUT above an ambient temperature; aging of the CUT; moisture in the immediate vicinity of the CUT; pressure in the immediate vicinity of the CUT above atmospheric pressure; physical stress on the CUT; semiconductor "burn-in", or irradiation of the CUT.

37. The method of claim 35 further comprising correcting for thermal drift by one of a reference conductor or a measurement of localized temperature.

* * * * *